(12) United States Patent
Remer et al.

(10) Patent No.: US 9,187,760 B2
(45) Date of Patent: Nov. 17, 2015

(54) PHARMACEUTICAL PRODUCT COMPRISING TRANSGENIC POLLEN EXPRESSING HETEROLOGOUS POLYPEPTIDES

(75) Inventors: Ricardo Amaral Remer, Rio de Janeiro (BR); Rogerio Margis, Rio de Janeiro (BR); Marcio Alves Ferreira, Rio de Janeiro (BR); Marcia Coronha Lima, Rio de Janeiro (BR)

(73) Assignee: Ricardo Amaral Remer, Rio de Janeiro (BR)

( * ) Notice: Subject to any disclaimer, the term of this patent is extended or adjusted under 35 U.S.C. 154(b) by 1231 days.

(21) Appl. No.: 10/595,610

(22) PCT Filed: Nov. 12, 2004

(86) PCT No.: PCT/BR2004/000224
§ 371 (c)(1),
(2), (4) Date: Jan. 28, 2008

(87) PCT Pub. No.: WO2005/046704
PCT Pub. Date: May 26, 2005

(65) Prior Publication Data
US 2010/0003286 A1 Jan. 7, 2010

(30) Foreign Application Priority Data
Nov. 13, 2003 (BR) .................................... 0305197

(51) Int. Cl.
*C12N 15/82* (2006.01)
*A61K 36/00* (2006.01)

(52) U.S. Cl.
CPC ............ *C12N 15/8257* (2013.01); *A61K 36/00* (2013.01)

(58) Field of Classification Search
None
See application file for complete search history.

(56) References Cited

U.S. PATENT DOCUMENTS

| 5,275,819 A | 1/1994 | Amer et al. |
| 2003/0182691 A1 * | 9/2003 | Robert et al. ................. 800/288 |

FOREIGN PATENT DOCUMENTS

| WO | WO 92/19229 A1 | 11/1992 | |
| WO | WO 99/49063 | * 9/1999 | ............. C12N 15/82 |
| WO | WO 02/099111 | * 12/2002 | ............. C12N 15/82 |
| WO | WO 02/099111 A2 | 12/2002 | |
| WO | WO 03/044050 | 5/2003 | |

OTHER PUBLICATIONS

DeOliveria et al. A. thaliana genes encoding glycine-rich proteins. (2002) GenBank Accession Z11858; pp. 1-8.*
First and Second Office Actions from the European Patent Office, along with the responses for corresponding EP application No. 04 797 141.1-2406.
Chinese Office Action, along with Notification of Grant of Patent issued in corresponding CN application No. 200480040363.2.

* cited by examiner

*Primary Examiner* — Cathy Kingdon Worley
(74) *Attorney, Agent, or Firm* — Laurence P. Colton; Smith Risley Tempel Santos LLC

(57) ABSTRACT

The present invention discloses pharmaceutical products useful for the treatment of allergies, autoimmune diseases, vaccination of mammals, as well as for in vitro diagnostics. These products preferably comprise pollen grains having altered protein composition by means of genetic modification in the plant that produces them. The production process of the present invention comprises the cultivation of genetically modified plants capable of producing pollen grains having modified molecular composition.

2 Claims, 8 Drawing Sheets

PHARMACEUTICAL PRODUCT COMPRISING TRANSGENIC POLLEN EXPRESSING HETEROLOGOUS POLYPEPTIDES

SEQUENCE LISTING

The instant application contains a Sequence Listing which has been submitted in ASCII format via EFS-Web and is hereby incorporated by reference in its entirety. Said ASCII copy, created on 30 Sep. 2013, is named 48220.001US_S-L.txt and is 10,747 bytes in size.

FIELD OF THE INVENTION

The present invention is related to pharmaceutical products and the production processes therefor. More specifically, this invention is related to pharmaceutical products comprising pollen grains having altered protein composition through genetic modification in the plant that produces them. The production processes of the pharmaceutical products of the present invention comprise the cultivation of genetically modified plants having pollen grains with altered molecular composition, making them useful for the treatment of allergies, autoimmune diseases, as well as the vaccination of eukaryotic organisms, and for in vitro diagnosis applications.

BACKGROUND OF THE INVENTION

The processes to obtain economically relevant compounds have been changing significantly in recent years in the area of biotechnology. Until recently, the traditional industrial fermentations, for instance, were the main technological option for the production of polypeptides, enzymes, antibiotics and other substances of economic interest. Meanwhile, as the knowledge about microbiology, biochemistry and genetics of the organisms involved in the fermentative processes increased, the production technologies have also been adapted and modified. The development of molecular biology techniques was remarkable in this context: besides offering tools for the understanding of the biochemical, genetic and evolutionary mechanisms of the many species studied, molecular biology also furthered the development of countless alternatives for the industrial production of substances, as a result of the combination possibilities of the different organism's characteristics.

The present-day market shows a great demand of products and processes in the Human and/or Animal Health segment and the interest in the development of technologies in this area continues. From the industrial technology standpoint, many factors can be considered as limiting or technological "bottlenecks". Especially relevant in the production of economically important substances are the costs involved in the purification, which frequently demands a series of complex and costly steps. The determination of the cost of new therapeutic products is a very complex process, if all phases involved are to be considered—from the product conception until its placement on the market. One major factor of impact on the costs is the adopted technology, especially in the case of biological products whose chemical synthesis has not yet been developed or which presents technical or economical disadvantages. The advance of the recombinant DNA technology allowed the production of proteins and other substances in virtually unlimited quantities. On the other hand, the expression system employed has a remarkable influence on the product's nature and on the production process. A good illustrative example is the production of the Tissue Plasminogen Activator (tPA), an anti-thrombotic agent used in the treatment of myocardium infarct, thrombosis and pulmonary embolism. This substance, when produced by *Escherichia coli*, or through the cultivation of genetically modified ovary cells from hamsters (CHO), presents significant differences regarding its structure (glycosilation, need of renaturing etc.) and production processes, which reflects on its price. In *E. coli*, 12% of the tPA's production costs correspond to the fermentative phase of the process and 88% are due to purification. On the other hand, in the production through CHO, 75% of the costs derive from the cellular cultivation and 25% from purification (Datar et al, "Process Economics of Animal Cells and Bacterial Fermentations: A Case Study Analysis of Tissue Plasminogen Activator" Bio/Technology 11:349-357, 1993). These differences are significant and can be decisively influent in the choice of the process to be used. Still other factors have a special importance in the choice of the production system, such as funds (capital) for the factory's installation, costs of raw materials, the need of qualified personnel (and its cost) as well as environmental and safety aspects.

The Vegetal Model

A safer and cheaper system to produce biologically originated substances may be idealized in transgenic plants cultivated in contained areas (greenhouses) or in agricultural areas. Furthermore, the vegetal system to produce substances of pharmaceutical interest offers various advantages, among which one might mention the absence of animal viruses and other animal cell products, as well as the absence of the typical contamination of bacterial fermentative processes, from yeasts or animal cells. In this context, the knowledge of the genetic and biochemical mechanisms of some vegetal models is reasonably wide, standing out, among other plants, *Arabidopsis thaliana*, *Nicotiana tabacum* and *Oryza sativa*. Among the main advantages of the use of the vegetal system for the production of substances with economical interest, one should emphasize the easier scale up, which is fundamental in the case of polypeptides and/or proteins of industrial interest. In the case of using microorganisms (recombinant or not), the phases involved in the scale up are normally the limiting factors of the process economy. This occurs for various reasons, among which the non-linearity of the determining relations of the process' efficiency (oxygen transfer, rheological factors, energy demand of the process etc.), the cost of the necessary production equipment and the need of adequately qualified personnel. In the case of the vegetal system, the mentioned cost components are much lower, since the scale-up tends to be simpler and linear. Besides that, in the evaluation of an industrial process' economy, the strategies seeking to eliminate the largest possible number of purification phases should be considered. Furthermore, plants are metabolically able to perform complex post-translational modifications, such as glycosylations, which widens the scope of possible peptides, antigens or vaccine candidates to be produced by plants. In this sense, the strategy of the present invention comprises the development of expression systems which take into account the most appropriate cellular and sub-cellular localizations for the desired products and, foremost, the elimination of purification steps.

The reproductive systems of *A. thaliana* and *N. tabacum* have been intensely studied in the recent years and are suitable to the logic of eliminating purification steps of the present invention. The starting point for the idealization of the present invention was the existing knowledge about the genes involved in the vegetal reproductive development and, more precisely, those related to the development of the tapetum which, for some years now, is the study object of the Laboratory for Plant Molecular Genetics of the Federal University of Rio de Janeiro, Brazil. Former studies in that laboratory in this area comprise the state of the art of the present invention. On one hand, the knowledge about the expression of the genes involved in the formation of *A. thaliana*'s inflorescence (Franco, MSc. Dissertation, UFRJ, 1992) was helpful to understand the function of the oleosin-type proteins, more recently studied with molecular biology techniques associated to microscopy (Ferreira, PhD Thesis, UFRJ, 1997). On the other hand, there also exists knowledge about the regulation mechanisms of the codifying genes of said oleosin-type proteins, studied with the help of the .beta.-glucuronidase (GUS) gene marker (Scholte, PhD Thesis, UFRJ, 1998). Even more recently, a strategy of modifying the protein composition of the external surface of pollen grains was described by Foster et al "Modifying the pollen coat protein composition in *Brassica*", Plant Journal 31(4): 477-486, 2002, also described in the document WO 99/49063, by the same authors. However, neither these, nor any other reference known by the author make any allusion or suggestion regarding the use of genetically modified plants for the production of pharmaceutical products in tissues and/or cells of the male vegetal reproductive system, neither do they mention the use of whole, intact, pollen grains derived from genetically modified plants as pharmaceutical products to be used in immunoreactions, as vaccines or as reactive agents for diagnostics, which collectively comprise the objects of the present invention.

For the purposes of the present invention, one should understand as "tissues and cells of the male vegetal reproductive system" the tissues or cells of the male vegetal reproductive system, including the anthers, tapetum, pollen—grains, parts and combinations thereof. For the purposes of the present invention, one should also understand as "immunoreactions" all reactions that involve cells and/or molecules of the immune system of eukaryotes, including vertebrates, invertebrates, mammals and the like, including mononuclear cells such as macrophages and lymphocytes B and T, neutrophils, eosinophils, besides antigens, antibodies, cytokines and other chemical mediators of the immune system, including parts of the same and its combinations. Furthermore, for the purposes of the present invention, one should understand as "heterologous polypeptide" any amino acid sequence which is not naturally produced by the plant, but whose synthesis in it derived from the genetic modification undertaken in the plant through the present invention. Without limiting the scope of the present invention, one should emphasize as being of special importance the use of pollen grains containing at least one heterologous polypeptide.

The present invention offers means to avoid some difficulties in both the production and use of polypeptides with therapeutic and/or diagnostics interest. On one hand, pollen grains are structurally stable, probably as a consequence of the need of reproductive success. Therefore, their "evolution" in order to resist the most diverse environmental stresses is useful to the logic of using them as a product, since their high stability is favorable and desirable. In an additional aspect, whole pollen grains of the present invention may be used in certain applications, bypassing the need of purification. As examples, herein used to illustrate the present invention but not to limit its scope, whole pollen grains containing heterologous polypeptides would permit: the direct use as antigens in the production of diagnostic kits, especially for screening, and its use as a vaccine preferably delivered onto mucous membranes or injected subcutaneously.

Pollen is often associated to allergy because some people develop symptoms such as sneezing, itching, cough, nasal irritation, eye watering and asthma when exposed to the pollen of certain plants. These particles are carried in large amounts by the air, normally during springtime. When they get in contact with the nasal mucous membranes or the throat, they may trigger allergic reactions known as polinosis or seasonal allergic rhinitis (for more details, consult Balda et al, "Tree-pollen Allergy is Efficiently Treated by Short-term Immunotherapy (STI) with Seven Preseasonal Injections of Molecular Standardized Allergens". *Allergy* 53, 740-748, 1998). As in any allergic process, the polinosis is a high sensibility to certain substances present in the pollen, and considerably varies from person to person, even though there seems to be a familiar correlation. In the majority of allergic reactions, the immune system responds to a "false alarm", mobilizing the attack against the allergen. The organism produces large quantities of specific IgEs, which bind themselves to the mastocytes in the tissues and to the basophils in the blood. When the allergen meets the IgE the liberation of histamine, prostaglandin, leucothriens and other substances occurs, thus causing the allergy symptoms (for more details, see Batanero et al, "IgE-binding and Histamine-release Capabilities of the Main Carbohydrate Component Isolated from the Major Allergen of Olive Tree Pollen, Ole e 1". *J Allergy Clin Immunol* 103, 147-153, 1999). Some strategies have been developed in order to obtain vaccines against autoimmune diseases and allergies, being generally based on the induction of tolerance. For example, known pollen grain allergens, when prepared in an encapsulated form, have shown to be efficient in the induction of tolerance by means of nasal administration. Nevertheless, the available encapsulating methods of allergens/antigens are laborious and costly, besides generally bringing about the denaturation of said allergens/antigens. The present invention's approach makes it possible to overcome these problems through the production of heterologous allergens/antigens in pollen grains.

Due to its natural ability to stimulate the production of specific IgEs and IgGs, we started from the hypothesis that the pollen could become a good candidate as a carrier and deliverer of vaccine antigens in mucous membranes, such as its direct use via nasal immunizations. Besides the already mentioned elevated structural stability of the pollen, an additional characteristic of the present invention under consideration is to enable the use of whole pollen grains as vaccines. Interestingly, one of the goals clearly expressed by the World Health Organization (WHO) is the development of new systems for the delivery of antigen vaccines to the respiratory tract. Furthermore, recent studies have demonstrated that vaccines derived from transgenic plants, when applied in the form of dry powder, seem to be the preferred solution for the lack of homogeneity in the concentrations of antigens produced in plants (for further references, see Sala et al., "Vaccine antigen production in transgenic plants: strategies, gene constructs and perspectives". *Vaccine* 21:803-808, 2003; Mielcarek et al. "Nasal vaccination using live bacterial vectors". *Advanced Drug Delivery Reviews* 51:55-69, 2001). On the other hand, the WHO's recommendation for the vaccine against tetanus (or lockjaw), for instance, is the administration of three consecutive doses of the respective antigen. This repeated administration has financial and logistical disadvantages, since some patients do not return for the second dose and because the vaccination campaigns have as a limiting factor: the need of a cold chain, considering that practically all vaccines are thermo labile. The availability of vaccines in pollen grains presents itself as capable of solving these mentioned problems, besides being easily delivered (without injections), easily standardized and endowed with an elevated thermal stability, being able to help avoid the logistics problems which are so far inherent to vaccination campaigns.

These advantages open up good perspectives for the study and development of this way of immunization in combination with the presentation form of the present invention.

Several efforts have been made in the last two decades in the sense of trying to develop subunit vaccines for human and veterinary use. The subunit vaccines are based on individual components derived from the infectious agent and, normally, have a low immunogenicity due to the absence of other cellular constituents from which they are often purified. Therefore, when developing vaccines it is desirable to plan the utilization of other substances which have the potential to increase the immune response to the antigens in question, what is normally done with the use of adjuvants. Entire cells or parts thereof can work as self-adjuvants, which is favorable for the present invention's approach. The identification of an appropriate antigen is only the first step in the development process to obtain a subunit vaccine, since adequate adjuvant systems and delivery systems of the respective antigen are also necessary. An adjuvant can be any material which increases the immune-humoral and/or cellular response to the antigen(s); it is generally accepted in literature that certain adjuvants act through the gradual liberation of the antigens to the cells of the immune system. Recent studies (Wiedermann, et al. "Modulation of an allergic immune response via the mucosal route in a murine model of inhalative type-I allergy" *Intl. Arch. Allergy Immunol.* 118:129-132, 1999) have shown that antigenic preparations in powdered form can also increase the incorporation of antigens by the antigen processing cells of the immune system. In this sense, the use of whole pollen grains, due to its powdered nature, offers this additional advantage in the case of application in vaccines. Independently of exactly knowing the specific mechanism involved, it is known that not only the cellular, but also the humoral immunity might be stimulated in various degrees, depending on the antigen, the adjuvant, the administration protocol and the species involved.

In order to develop an effective and commercially feasible vaccine, the relation between the production cost and the large-scale production capacity of the antigenic preparation and the adjuvant system should be taken into account. On the other hand, the growing number of vaccines under developed and the number of required injections for a wide-ranging immunization program for children, for instance, generates elevated costs and the preoccupation about the discontinuity potential of current vaccination programs. This makes highly desirable the availability of alternative immunization means, especially those allowing the so-called multivalent vaccination, that is, the one that permits to present multiple antigens or epitopes simultaneously. In this context, transgenic plants have been the object of several attempts to obtain "edible" vaccines, due to their notorious advantages in terms of production costs and administration. However, vaccines produced in transgenic plants destined for oral consumption have the disadvantage of passing by the gastrointestinal barrier, which destroys a significant portion of the vaccine antigens. For that reason, the state of the art shows that the amount of antigens required for an effective immune response derived from an edible transgenic plant vaccine is from 100 to 1,000 times higher than the amount of antigens necessary for an effective parenteral immunization (for further reference, see Carter III, J. E., and Langridge, W. H. R. "Plant-based vaccines for protection against infectious and autoimmune diseases". *Critical Reviews in Plant Sciences* 21(2), 93-109, 2002; Streatfield and Howard "Plant-based vaccines". *International Journal for Parasitology* 33, 479-493, 2003). Therefore, the need to develop new alternatives to overcome these difficulties persists.

The entry route of most pathogenic agents is the mucous surfaces and a large part of the infections is located in the mucous and sub mucous tissues. However, conventional injectable vaccines are poorly efficient for the induction of an immune response in mucous membranes. As a consequence, several experiments are being carried out in order to offer alternatives for the immunization in mucous membranes, which includes, for instance, the incorporation of antigens in larger particles (such as liposomes, immune stimulatory complexes, microspheres) for increasing the efficiency of the immune response in mucous tissues. On the other hand, the use of adequate adjuvants is normally very important for the stimulation of the desired type of immune response. Among the known adjuvants, and in the scope of the present invention, one might point out the vegetable oils. A primary advantage of the use of vegetable oil adjuvants over the use of mineral oils is that vegetable oils can be easier metabolized and are, therefore, more tolerable. Patent literature is rich in examples of the use of vegetable oils as adjuvants in vaccines, including, for instance, documents WO 01/95934 "The use of plant oil-bodies in vaccine delivery systems" and WO 02/00169 "Production of vaccines using transgenic plants or modified plant viruses as expression vectors and transencapsidated viral coat proteins as epitope presentation systems". Most of these patents disclose formulations and the use of water-in-oil or oil-in-water emulsions which are prepared through the mixture of pure chemical compounds. However, none of the mentioned documents reveals or suggests the use of tissues or cells from the male vegetal reproductive system, such as whole pollen grains, or even parts thereof, as an useful pharmaceutical product in immune reactions or as an antigen-adjuvant combination for immunization, preferably applicable in mucous membranes. In this context, the present invention offers a technical and commercially feasible production alternative of a pharmaceutical product which is potentially useful in the treatment of dysfunctions of the immune system of eukaryotes and which allows, among other characteristics, the production of multiple substances in one single system.

SUMMARY OF THE INVENTION

Having in mind the prior art limitations and all the above-mentioned reports, the present invention provides pharmaceutical products as well as their production process in genetically modified plants. The products of the present invention comprise tissues and/or cells of the male vegetal reproductive system, including bioactive substances to be used in Human and/or Animal Health.

In one aspect, the present invention provides a production process of pharmaceutical products which overcome difficulties in the production, distribution, storage and logistics of said products. In another aspect, the present invention offers a production process of pharmaceutical products to be used as immune reactions, through the expression, in male vegetal reproductive tissues, of marking genes, codifying genes of antigens and/or therapeutic polypeptides. In yet another aspect, the pharmaceutical products of the present invention are useful in the immune modulation of eukaryotes, including mammals and other vertebrates as well as invertebrates such as insects and the like. From an additional point of view, the pharmaceutical products of the present invention are potentially useful in immune diagnostic reactions. These and other aspects constitute the objects of the present invention and will

DETAILED DESCRIPTION OF THE INVENTION

Figure 1:
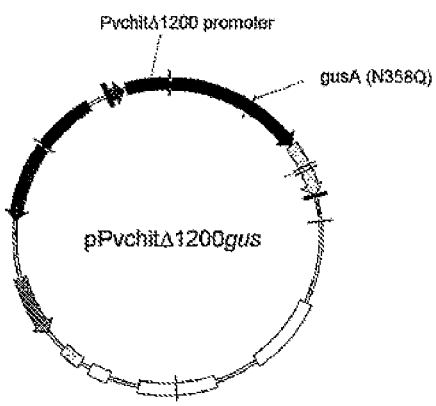
FIG. 1 is a schematic representation of the binary plasmid pPvchitΔ1200gus, used as vector for the reporter gene GUS under the control of part (−1200) of the bean chitinase promoter.
Figure 4:
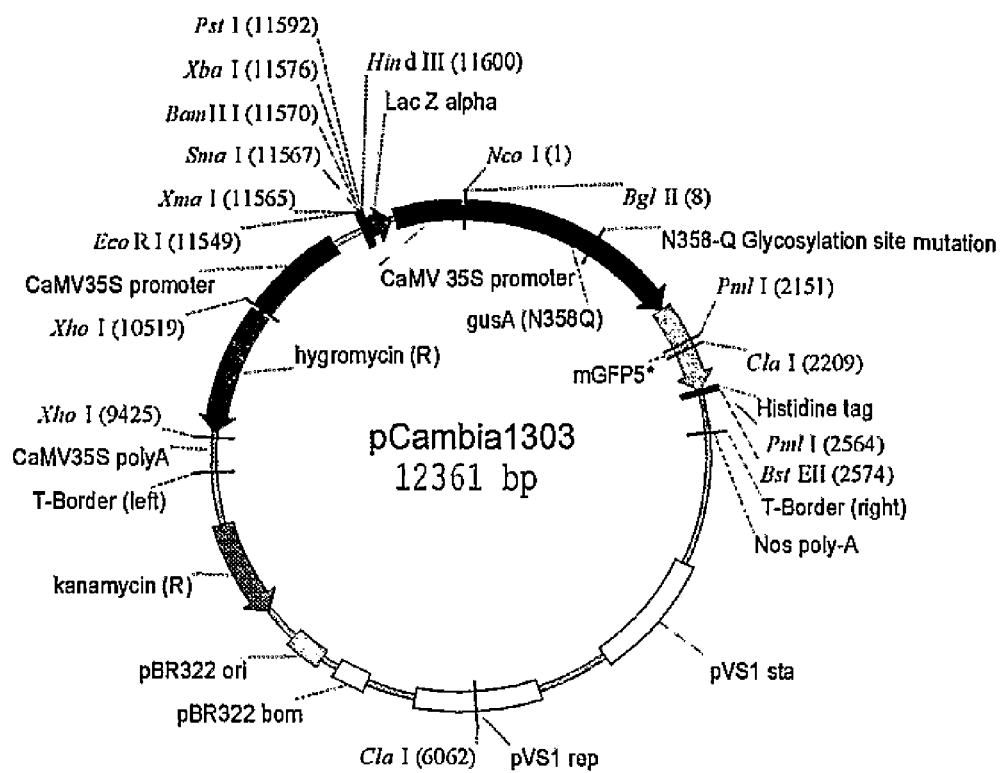
FIG. 4 is a schematic representation of binary plasmid pCambia 1303, used as vector having the reporter genes GFP, GUS and of the selection markers for Kanamicin and hygromicin. Single restriction sites XbaI and NcoI and other single and double restriction sites are also indicated.
Figure 6:
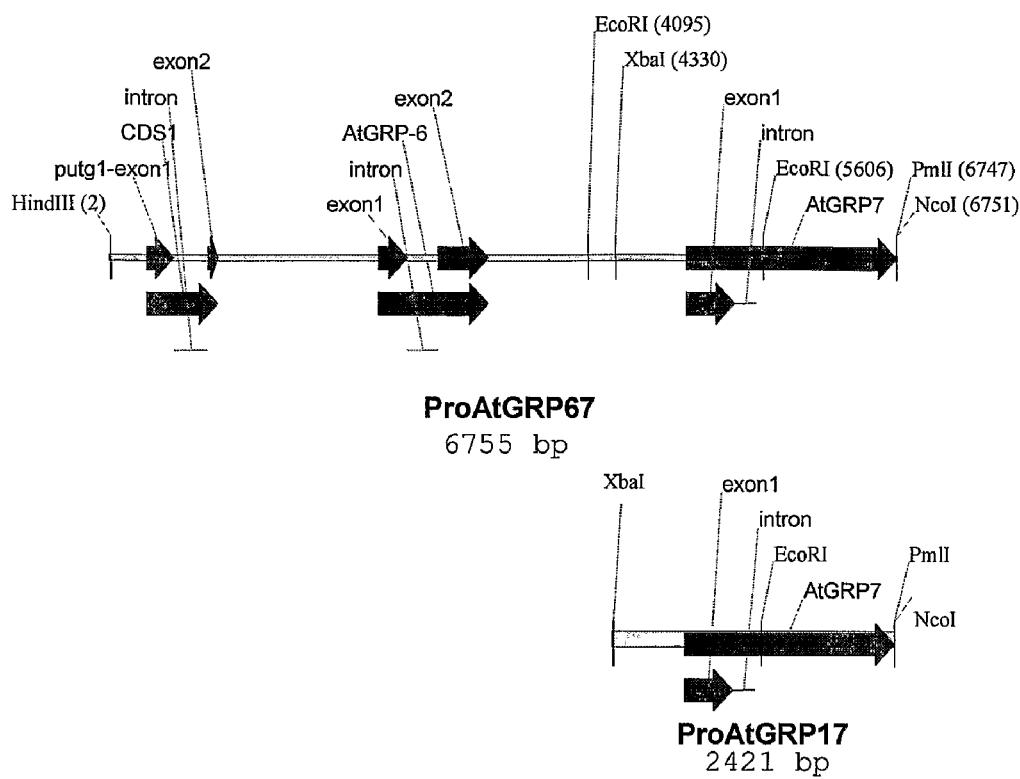
FIG. 6 is a schematic representation of the ProAtGRP67 region obtained by PCR and the fragment ProAtGRP17 generated by cleavage with XbaI and NcoI enzymes. In the latter the shorter arrow indicates the relative position of exon 1 and the intron.

In order to evaluate the applicability of the use of tissues and cells from the male vegetal reproductive system as pharmaceutical products, we evaluated situations which could be considered to be most critical to said use. Therefore, the tested applications, even though not limiting the scope of the present invention, are herein presented as the use of whole pollen grains as vaccines, immunotherapic agents and/or diagnostics reagents. In order to achieve this goal, genetic constructions were developed aiming to allow the expression of a reporter gene in such a way that its presence in plant subcellular structures and in pollen grains could be more easily analyzed. Different genetic constructions containing the reporter gene GUS (codifier of the β-glucuronidase enzyme) were evaluated: (i) the binary vector pDE1001 for the transformation of *N. tabacum* plants containing the reporter gene GUS under the control of the promoter PvChit (promoter of the bean chitinase, *Phaseolus vulgaris*, the genetic construction of which was detailed in Lima et al., (2002) Bean class IV chitinase promoter is modulated during plant development and under abiotic stress. *Physiologia Plantarum* 116:512-521, in a construction herein called pPvchitΔ1200gus, FIG. 1), which allows the intracellular expression of the glucuronidase (GUS) enzyme in tobacco pollen grains; and (ii) the binary vector for the transformation of plants pCambia 1303 (FIGS. 4 and 6) as the receptor of the in-frame fusion SEQ ID NO. 1-GUSGFP under the control of the promoter SEQ ID NO. 2 (formerly called AtGRP7 by de Oliveira et al. "Inflorescence-specific genes from *Arabidopsis thaliana* encoding glycine-rich proteins". Plant J. 3:495-507, 1993). This last construction aims to permit the expression of the fusion SEQ ID NO. 3-GUSGFP on the surface of pollen grains, in order to allow the testing of the pollen grains hereby obtained for the applications of the present invention.

EXAMPLE 1

Obtaining "WT" and "GM" Tobacco Pollen Grains

Figure 2:
FIG. 2 is a photograph of a tobacco flower, clearly showing the anthers.

Wild tobacco plants (*N. tabacum*) from the SR1 lineage, referred to as "WT" in the present invention, and also tobacco plants transformed with the vector pPvchitΔ1200gus (FIG. 1), available from a previous study (Viviane Moreira, PhD Thesis, UFRJ, 2002, also described in Lima et al., "Bean class IV chitinase promoter is modulated during plant development and under abiotic stress". *Physiologia Plantarum* 116:512-521, 2002) were cultivated in a greenhouse until the blossoming of mature flowers. The genetically modified lineage of tobacco in the present invention is referred to as "GM", and produces pollen grains with an altered composition, containing the GUS enzyme in its interior. The following procedure was adopted in order to collect the pollen grains: as soon as the dehiscence occurred, the entire flowers (FIG. 2) were removed from the WT and GM plants and the intact anthers were transferred into Eppendorf tubes with the help of a scalpel. The average weight of the pollen grains present in each inflorescence was weighted with an analytical scale. Taking into account the difference between the total weight with anthers and the total weight without anthers (after homogenization and the subsequent removal of the pollen grains present in said anthers), the average weight of pollen grains present in each flower was equal to 1 milligram—consequently, the equivalent of 0.2 milligram for each anther, since one *N. tabacum* flower has 5 (five) anthers.

EXAMPLE 2

Evaluation of GUS Stability in "GM" Pollen Grains

The stability of pollen grains maintained at room temperature (about 25 degrees Celsius) was evaluated qualitatively through the verification of the activity of the β glucuronidase (GUS) enzyme in the GM pollen grains. In order to do so, colorimetrical reactions were performed using 1 µL of the compound X Gluc in 100 µL of phosphate buffer 0.1 M pH 7 and whole transgenic pollen grains containing the GUS enzyme. In the tests performed in laboratory, the activity of the GUS enzyme was kept in stock for at least one year at room temperature. In this context, it is worthwhile to emphasize that the physico-chemical conditions necessary for the maintenance of an enzyme's activity are much more restricted than the conditions necessary to maintain the immunogenicity of a polypeptide sequence. Therefore, these results suggest an elevated stability of heterologous peptides expressed in the pollen grains of $N.$ $tabacum$ "GM", which is desirable within the scope of applications of the present invention.

Analysis of the Immune Response of Rats to Tobacco Pollen Grains

Since the present invention relates to new production technologies and formulations of pharmaceutical products especially applicable in immune reactions, such as immune modulators, vaccines and diagnosis reagents, the immunoreactivity of pollen grains under different conditions is the starting point for the evaluation of its applicability. The approach used herein includes the study of the immune response of female Wistar rats ($Ratus$ $novergicus$), submitted to different ways of pollen grain exposures.

The potential of pollen grains to induce inflammation was evaluated by analyzing different administration schedules of WT tobacco pollen grains in rats. The cellular responses of animals submitted to different exposure/sensitizing schemes were monitored by counting the amount of cells present in broncho-alveolar lavage or in pleural fluid and checking the appearance of paw edemas, while the molecular responses were monitored through the observation of protein extravasation, measurement of the total serological IgE and IgG concentrations through ELISA, and of specific serological IgGs against pollen grain proteins by Western Blot.

Groups of 3 to 6 animals, as indicated, were submitted to the administration of different regimes of saline solution suspensions containing WT or GM tobacco pollen grains, in the concentrations of 0.5, 50 and 500 µg per animal (concentrations based on the average weight of 1 mg of pollen per tobacco flower), with or without the joint administration of aluminum hydroxide (5 mg per animal) as adjuvant. The verification of the occurrence or not of any inflammation in the broncho-alveolar cavity or the pleural cavity was done respectively through broncho-alveolar or pleural washing, followed by the total leucocytes count in a Neubauer chamber and a relative count of monocytes, neutrophils and eosinophils after centrifugation on a glass slide. Both counts were carried out with the help of an optical microscope. As will become shown in the following experiments, none of the tested conditions caused a significant alteration of cell counts consistent with an inflammatory process. Additionally, none of the tested conditions produced significant alteration of the protein exudates, which would be typical of an inflammatory process. Serum samples of the animals submitted to the different experimental conditions were collected and stored for later molecular analysis. And again, none of the pollen grain administration conditions tested showed a significant increase of the total serological IgE and IgG concentrations, according to quantitative measurements through ELISA. The results of the following tables show that none of the different pollen grain administration conditions caused detectable allergic/inflammatory type reactions in animals.

EXAMPLE 3

Immune Response of Rats Submitted to a Single Intrapleural Injection

TABLE 1

Experimental conditions of pollen grain exposure to $R.$ $novergicus$ Wistar rats and their respective results. The animals were submitted to an intrapleural injection of 5 µg of wild tobacco pollen grains (100 µL in saline solution). The chart shows the cell counts in pleural lavage 4 hours after the procedure.

| N | CAM Leu tot | Mono % | Eos % | Neut % | Mono Millions | Eos Millions | Neut Millions |
|---|---|---|---|---|---|---|---|
| 1 | 17 | 85 | 15 | 0 | 4.34 | 0.77 | 0 |
| 2 | 25 | 83 | 17 | 0 | 6.23 | 1.28 | 0 |
| 3 | 16 | 85 | 15 | 0 | 4.08 | 0.72 | 0 |
| Average |  |  |  |  | 4.88 | 0.92 | 0 |
| Deviation |  |  |  |  | 1.17 | 0.31 | 0 |
| E.P.M |  |  |  |  | 0.83 | 0.22 | 0 |

Subtitle abbreviations:
CAM Leu tot (total leucocytes counted in a Neubauer chamber);
Mono % (% of monocytes);
Eos % (% of eosinophils);
Neut % (% of neutrophils);
E.P.M. (mean standard error).

TABLE 2

Experimental conditions of pollen grain exposure to $R.$ $novergicus$ Wistar rats and their respective results. The animals were submitted to an intrapleural injection of 50 µg of wild tobacco pollen grains (100 µL in saline solution). The chart shows the cell counts in pleural lavage 4 hours after the procedure.

| N | CAM Leu tot | Mono % | Eos % | Neut % | Mono Millions | Eos Millions | Neut Millions |
|---|---|---|---|---|---|---|---|
| 1 | 17 | 86 | 14 | 0 | 4.39 | 0.71 | 0 |
| 2 | 12 | 78 | 22 | 0 | 2.81 | 0.79 | 0 |
| 3 | 17 | 88 | 11 | 1 | 4.49 | 0.56 | 0.05 |
| Average |  |  |  |  | 3.89 | 0.69 | 0.02 |
| Deviation |  |  |  |  | 0.94 | 0.12 | 0.03 |
| E.P.M |  |  |  |  | 0.67 | 0.08 | 0.02 |

TABLE 3

Experimental conditions of pollen grain exposure to $R.$ $novergicus$ Wistar rats and their respective results. The animals were submitted to an intrapleural injection of 500 µg of wild tobacco pollen grains (100 µL in saline solution). The chart shows the cell counts in pleural lavage 4 hours after the procedure.

| N | CAM Leu tot | Mono % | Eos % | Neut % | Mono Millions | Eos Millions | Neut Millions |
|---|---|---|---|---|---|---|---|
| 1 | 20 | 82 | 18 | 0 | 4.92 | 1.08 | 0 |
| 2 | 21 | 81 | 19 | 0 | 5.10 | 1.20 | 0 |
| 3 | 23 | 89 | 11 | 0 | 6.14 | 0.76 | 0 |
| Average |  |  |  |  | 5.39 | 1.01 | 0 |
| Deviation |  |  |  |  | 0.66 | 0.23 | 0 |
| E.P.M |  |  |  |  | 0.47 | 0.16 | 0 |

The results of tables 1-3 show that in none of the tested conditions a statistically significant alteration of the cell counts in pleural lavage occurred, indicating that the administration of pollen grains under these conditions does not induce the characteristic inflammatory response of allergies. In view of these results, a new battery of experiments was conducted by using a larger number of animals and a higher exposure to the pollen grains.

EXAMPLE 4

Immune Response of Rats Submitted to Consecutive Intrapleural Injections

TABLE 4

Experimental conditions of pollen grain exposure to *R. novergicus* Wistar rats and their respective results. Saline solution intrapleural injection (as control, 100 µL per animal) in three consecutive exposures with an interval of one week between each exposure. The chart shows the cell counts in pleural lavage 4 hours after the procedure by intrapleural injection of 5 µg of pollen grains in a volume of 100 µL per animal.

| N | CAM Leu tot | Mono % | Eos % | Neut % | Mono Millions | Eos Millions | Neut Millions |
|---|---|---|---|---|---|---|---|
| 1 | 44 | 78 | 3 | 19 | 11.67 | 0.45 | 2.84 |
| 2 | 30 | 78 | 17 | 5 | 7.02 | 1.53 | 0.45 |
| 3 | 24 | 77 | 16 | 7 | 5.54 | 1.15 | 0.50 |
| Average | | | | | 8.08 | 1.04 | 1.27 |
| Deviation | | | | | 3.20 | 0.55 | 1.37 |
| E.P.M | | | | | 2.26 | 0.39 | 0.97 |

TABLE 5

Experimental conditions of pollen grain exposure to *R. novergicus* Wistar rats and their respective results. Intrapleural injection of 5 µg of wild tobacco pollen grains (in saline solution injection of 100 µL per animal) in three consecutive exposures with an interval of one week between each exposure. The chart shows the cell counts in pleural lavage 4 hours after the procedure by intrapleural injection of 5 µg of pollen grains in a volume of 100 µL per animal.

| N | CAM Leu tot | Mono % | Eos % | Neut % | Mono Millions | Eos Millions | Neut Millions |
|---|---|---|---|---|---|---|---|
| 1 | 27 | 85 | 13 | 2 | 6.89 | 1.05 | 0.16 |
| 2 | 45 | 77 | 8 | 15 | 10.40 | 1.08 | 2.03 |
| 3 | 52 | 64 | 11 | 25 | 11.32 | 1.94 | 4.42 |
| 4 | 85 | 69 | 8 | 23 | 19.94 | 2.31 | 6.65 |
| Average | | | | | 12.13 | 1.60 | 3.31 |
| Deviation | | | | | 5.54 | 0.63 | 2.82 |
| E.P.M | | | | | 3.20 | 0.36 | 1.63 |

TABLE 6

Experimental conditions of pollen grain exposure to *R. novergicus* Wistar rats and their respective results. Intrapleural injection of 50 µg of wild tobacco pollen grains (in saline solution injection of 100 µL per animal) in three consecutive exposures with an interval of one week between each exposure. The chart shows the cell counts in pleural lavage 4 hours after the procedure by intrapleural injection of 50 µg of pollen grains in a volume of 100 µL per animal.

| N | CAM Leu tot | Mono % | Eos % | Neut % | Mono Millions | Eos Millions | Neut Millions |
|---|---|---|---|---|---|---|---|
| 1 | 50 | 68 | 14 | 18 | 10.20 | 2.10 | 2.70 |
| 2 | 37 | 69 | 14 | 17 | 7.66 | 1.55 | 1.89 |
| 3 | 145 | 71 | 16 | 13 | 37.06 | 8.35 | 6.79 |
| 4 | 36 | 81 | 10 | 9 | 8.75 | 1.08 | 0.97 |
| Average | | | | | 15.92 | 3.27 | 3.09 |
| Deviation | | | | | 14.13 | 3.41 | 2.57 |
| E.P.M | | | | | 8.16 | 1.97 | 1.48 |

TABLE 7

Experimental conditions of pollen grain exposure to *R. novergicus* Wistar rats and their respective results. Intrapleural injection of 500 µg of wild tobacco pollen grains (in saline solution injection of 100 µL per animal) in three consecutive exposures with an interval of one week between each exposure. The chart shows the cell counts in pleural lavage 4 hours after the procedure by intrapleural injection of 500 µg of pollen grains in a volume of 100 µL per animal.

| N | CAM Leu tot | Mono % | Eos % | Neut % | Mono Millions | Eos Millions | Neut Millions |
|---|---|---|---|---|---|---|---|
| 1 | 67 | 77 | 7 | 16 | 19.60 | 1.78 | 4.07 |
| 2 | 86 | 55 | 7 | 38 | 16.08 | 2.05 | 11.11 |
| 3 | 136 | 56 | 17 | 27 | 30.46 | 9.25 | 14.69 |
| 4 | 147 | 43 | 4 | 53 | 25.28 | 2.35 | 31.16 |
| Average | | | | | 22.86 | 3.86 | 15.26 |
| Deviation | | | | | 6.33 | 3.60 | 11.48 |
| E.P.M. | | | | | 3.66 | 2.08 | 6.63 |

Figure 3:
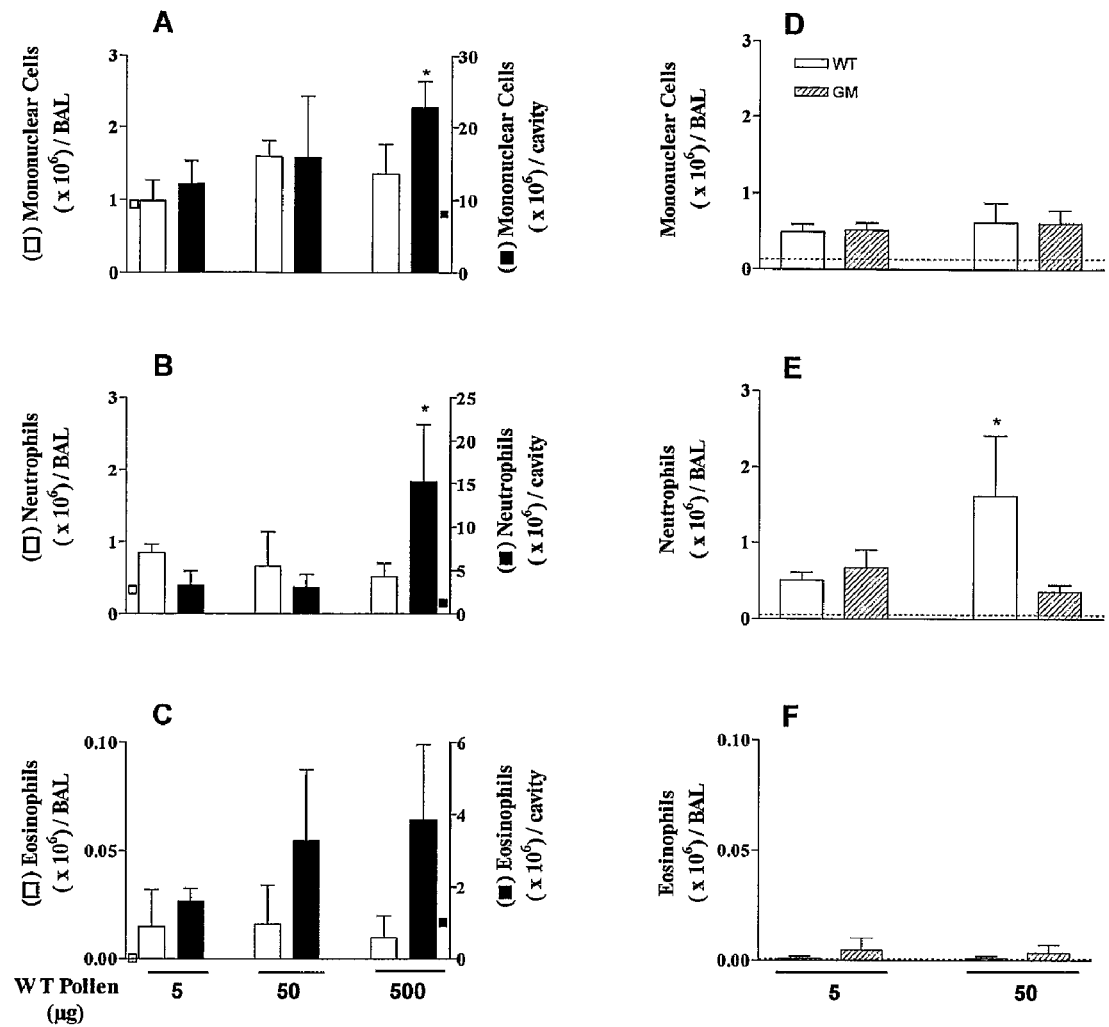
FIG. 3 are counts of mononuclear cells A), neutrophils B), and eosinophils C), in alveolar lavage (BAL) of rats subjected to three consecutive instillations of pollen grains in the indicated concentrations and in pleural lavage of rats subjected to intrapleural injections of pollen grains in the same concentrations. □ and ■ represent, respectively, the average values of BAL and pleural controls. C), D), and F) represent, respectively, the counts of mononuclear cells, neutrophils and eosinophils of broncho-alveolar lavage of rats subjected to three consecutive instillations of WT or GM pollen grains in the indicated concentrations. Dashed lines represent the average values of the controls instilled with saline solution. Columns represent averages±E. P. M. and asterisks indicate statistically significant differences (p<0.05).

The results of tables 4-7 show that there was no statistically significant alteration of the cell counts in pleural lavage under the conditions of consecutive administrations of 5 and 50 µg of pollen grains. In the condition of administrating 500 µg of pollen grains there was a significant increase in the counts of mononuclear cells and neutrophils, as well as an increase (even though statistically not significant) of eosinophils. These results are also shown in FIG. 3, panels A, B and C, respectively. The observed increase of the cell counts in the animals submitted to the administration of 500 µg of pollen grains demonstrates that the animals are responsive only to extreme concentrations of said pollen grains. However, the intrapleural administration of pollen grains in the concentration range of up to 50 µg per animal, in 3 consecutive applications did not induce detectable inflammatory-type response which is typical of allergies. Since the typical conditions of intrapleural administration of antigens very rarely exceed a concentration of 20 µg per animal, these results show that intrapleural pollen grain injections could be, surprisingly, employed in immunization or immunotherapy programs for animals, without hereby inducing the appearance of typical allergic/inflammatory symptoms. In order to verify the response of animals submitted to intranasal administration of pollen grains, another set of experiments was performed, as shown in the tables below.

EXAMPLE 5

Immune Response of Rats Submitted to Two Consecutive Intranasal Instillations

TABLE 8

Experimental conditions of pollen grain exposure to *R. novergicus* Wistar rats and their respective results. Intranasal instillation of saline solution (as a control, 50 µL per nostril per animal) in two consecutive exposures with an interval of one week between each exposure. The chart shows the cell counts in broncho-alveolar lavage of normal animals, 4 hours after the last instillation.

| N | CAM Leu tot | Mono cont. | Eos cont. | Neut cont. | Mono thousands | Eos Thous. | Neut Thous. |
|---|---|---|---|---|---|---|---|
| 1 | 74 | 73 | 9 | 18 | 1351 | 167 | 333 |
| 2 | 28 | 89 | 0.5 | 10.5 | 623 | 4 | 74 |
| 3 | 45 | 99 | 1 | 0 | 1114 | 11 | 0 |
| 4 | 26 | 30 | 0 | 70 | 195 | 0 | 455 |
| Average | | | | | 820.6 | 45.3 | 215.4 |
| Deviation | | | | | 515.5 | 80.9 | 214.3 |
| E.P.M. | | | | | 297.6 | 46.7 | 123.7 |

TABLE 9

Experimental conditions of pollen grain exposure to *R. novergicus* Wistar rats and their respective results. Intranasal instillation of 5 μg of wild tobacco pollen grains (in saline solution, instillation of 50 μL per nostril per animal) in two consecutive exposures with an interval of one week between each exposure. The chart shows the cell counts in broncho-alveolar lavage 4 hours after the last intranasal instillation.

| N | CAM Leu tot | Mono % | Eos % | Neut % | Mono Thous. | Eos Thous. | Neut Thous. |
|---|---|---|---|---|---|---|---|
| 1 | 127.5 | 54 | 23 | 23 | 1721 | 701 | 765 |
| 2 | 64 | 70 | 0 | 30 | 1120 | 0 | 480 |
| 3 | 81 | 71 | 0 | 29 | 1438 | 0 | 587 |
| 4 | 41 | 97 | 0 | 3 | 994 | 0 | 31 |
| 5 | 38.5 | 85 | 0 | 15 | 818 | 0 | 144 |
| Average | | | | | 1218.3 | 140.3 | 401.5 |
| Deviation | | | | | 360.9 | 313.6 | 306.7 |
| E.P.M. | | | | | 180.5 | 156.8 | 153.4 |

TABLE 10

Experimental conditions of pollen grain exposure to *R. novergicus* Wistar rats and their respective results. Intranasal instillation of 50 μg of wild tobacco pollen grains (in saline solution, instillation of 50 μL per nostril per animal) in two consecutive exposures with an interval of one week between each exposure. The chart shows the cell counts in broncho-alveolar lavage 4 hours after the last intranasal instillation.

| N | CAM Leu tot | Mono % | Eos % | Neut % | Mono Thous. | Eos Thous. | Neut Thous. |
|---|---|---|---|---|---|---|---|
| 1 | 223 | 46 | 0 | 54 | 2565 | 0 | 3011 |
| 2 | 147 | 62 | 1 | 38 | 2279 | 37 | 1397 |
| 3 | 37 | 95 | 0 | 5 | 879 | 0 | 46 |
| 4 | 30 | 97 | 0 | 3 | 728 | 0 | 23 |
| 5 | 68 | 100 | 0 | 0 | 1700 | 0 | 0 |
| Average | | | | | 1629.9 | 7.4 | 895.2 |
| Deviation | | | | | 943.7 | 18.4 | 1323.8 |
| E.P.M. | | | | | 409.1 | 8.2 | 661.9 |

TABLE 11

Experimental conditions of pollen grain exposure to *R. novergicus* Wistar rats and their respective results. Intranasal instillation of 500 μg of wild tobacco pollen grains (in saline solution, instillation of 50 μL per nostril per animal) in two consecutive exposures with an interval of one week between each exposure. The chart shows the cell counts in broncho-alveolar lavage 4 hours after the last intranasal instillation.

| N | CAM Leu tot | Mono % | Eos % | Neut % | Mono Thous. | Eos Thous. | Neut Thous. |
|---|---|---|---|---|---|---|---|
| 1 | 68.5 | 70 | 0 | 30 | 1199 | 0 | 514 |
| 2 | 48 | 77 | 0 | 23 | 924 | 0 | 276 |
| 3 | 86 | 62 | 0 | 38 | 1333 | 0 | 817 |
| 4 | 135 | 62.5 | 0 | 37.5 | 2109 | 0 | 1266 |
| Average | | | | | 1391.3 | 0 | 718.1 |
| Deviation | | | | | 508.1 | 0 | 426.9 |
| E.P.M. | | | | | 293.3 | 0 | 246.5 |

EXAMPLE 6

Immune Response of Rats Submitted to Three Consecutive Intranasal Instillations

TABLE 12

Experimental conditions of pollen grain exposure to *R. novergicus* Wistar rats and their respective results. Intranasal instillation of saline solution (as a control, 50 μg per nostril, per animal) in three consecutive exposures with an interval of one week between each exposure. The chart shows the cell counts in broncho-alveolar lavage of normal animals.

| N | CAM Leu tot | Mono % | Eos % | Neut % | Mono Thous. | Eos Thous. | Neut Thous. |
|---|---|---|---|---|---|---|---|
| 1 | 49 | 83 | 0 | 17 | 1017 | 0 | 208 |
| 2 | 35 | 96 | 0 | 4 | 840 | 0 | 35 |
| 3 | 69 | 59 | 0 | 41 | 1018 | 0 | 707 |
| 4 | 47 | 84 | 0 | 6 | 987 | 0 | 71 |
| 5 | 58 | 57 | 0 | 43 | 827 | 0 | 624 |
| Average | | | | | 937.6 | 0 | 328.9 |
| Deviation | | | | | 96.2 | 0 | 315.3 |
| E.P.M. | | | | | 48.1 | 0 | 157.6 |

TABLE 13

Experimental conditions of pollen grain exposure to *R. novergicus* Wistar rats and their respective results. Intranasal instillation of 5 μg of wild tobacco pollen grains (in saline solution, instillation of 50 μL per nostril, per animal) in three consecutive exposures with an interval of one week between each exposure. The chart shows the cell counts in broncho-alveolar lavage 4 hours after the last intranasal instillation.

| N | CAM Leu tot | Mono cont. | Eos cont. | Neut cont. | Mono Thous. | Eos Thous. | Neut Thous. |
|---|---|---|---|---|---|---|---|
| 1 | 79 | 53 | 0 | 47 | 1047 | 0 | 928 |
| 2 | 60 | 60 | 4 | 36 | 900 | 60 | 540 |
| 3 | 53.6 | 31 | 0 | 69 | 415 | 0 | 925 |
| 4 | 103 | 62 | 0 | 38 | 1597 | 0 | 979 |
| Average | | | | | 989.7 | 15 | 842.8 |
| Deviation | | | | | 486.3 | 30 | 203.4 |
| E.P.M. | | | | | 280.7 | 17.3 | 117.4 |

TABLE 14

Experimental conditions of pollen grain exposure to *R. novergicus* Wistar rats and their respective results. Intranasal instillation of 50 μg of wild tobacco pollen grains (in saline solution, instillation of 50 μL per nostril, per animal) in three consecutive exposures with an interval of one week between each exposure. The chart shows the cell counts in broncho-alveolar lavage 4 hours after the last intranasal instillation.

| N | CAM Leu tot | Mono % | Eos % | Neut % | Mono Thous. | Eos Thous. | Neut Thous. |
|---|---|---|---|---|---|---|---|
| 1 | 119 | 37 | 0 | 63 | 1101 | 0 | 1874 |
| 2 | 93 | 88 | 0 | 12 | 2046 | 0 | 279 |
| 3 | 66 | 97 | 0 | 3 | 1601 | 0 | 50 |
| 4 | 86 | 77 | 3 | 20 | 1656 | 65 | 430 |
| Average | | | | | 1600.7 | 16.1 | 658.2 |
| Deviation | | | | | 387.8 | 32.3 | 825.7 |
| E.P.M. | | | | | 223.9 | 18.6 | 476.7 |

TABLE 15

Experimental conditions of pollen grain exposure to *R. novergicus* Wistar rats and their respective results. Intranasal instillation of 500 μg of wild tobacco pollen grains (in saline solution, instillation of 50 μL per nostril, per animal) in three consecutive exposures with an interval of one week between each exposure. The chart shows the cell counts in broncho-alveolar lavage 4 hours after the last intranasal instillation.

| N | CAM Leu tot | Mono % | Eos % | Neut % | Mono Thous. | Eos Thous. | Neut Thous. |
|---|---|---|---|---|---|---|---|
| 1 | 83 | 50 | 0 | 50 | 1038 | 0 | 1038 |
| 2 | 90 | 82 | 0 | 18 | 1845 | 0 | 405 |
| 3 | 104 | 98 | 0 | 2 | 2548 | 0 | 52 |
| 4 | 53 | 47 | 0 | 53 | 623 | 0 | 702 |
| 5 | 45 | 66 | 0 | 34 | 743 | 0 | 383 |
| Average | | | | | 1359.2 | 0 | 515.9 |
| Deviation | | | | | 817.8 | 0 | 371.5 |
| E.P.M. | | | | | 408.9 | 0 | 185.8 |

The results of tables 12-15 show that in none of the tested conditions a statistically significant alteration of the cell counts in broncho-alveolar lavage occurred, indicating that the administration of pollen grains under these conditions does not induce detectable allergic-type inflammatory response. In view of these results, a new set of experiments was conducted involving a larger number of animals and higher concentrations of pollen grains. These results are also presented in FIG. 3, panels A, B and C, respectively, which clearly show that there was no statistically significant alteration of the cell counts in pleural lavage under the consecutive administration conditions of 5, 50 and 500 μg of pollen grains.

EXAMPLE 7

Immune Response of Rats Subjected to Subcutaneous Injection, Followed by a "Booster"—Challenge with 10 μg of Pollen Grains in the Pleural Cavity

TABLE 16

Experimental conditions of pollen grain exposure to *R. novergicus* Wistar rats and their respective results. The chart shows the cell counts in pleural lavage of normal animals, which were not submitted to any program of sensitizing or challenge.

| N | CAM Leu tot | Mono % | Eos % | Neut % | Mono Millions | Eos Millions | Neut Millions |
|---|---|---|---|---|---|---|---|
| 1 | 39 | 87 | 12 | 1 | 11.5 | 1.6 | 0.1 |
| 2 | 34 | 81 | 19 | 0 | 8.3 | 1.9 | 0 |
| 3 | 26 | 89 | 11 | 0 | 7.4 | 0.9 | 0 |
| 4 | 33 | 77 | 23 | 0 | 7.6 | 2.3 | 0 |
| 5 | 40 | 86 | 13 | 1 | 11.7 | 1.8 | 0.1 |
| Average | | | | | 9.3 | 1.70 | 0.05 |
| Deviation | | | | | 2.13 | 0.51 | 0.07 |
| E.P.M. | | | | | 1.07 | 0.25 | 0.04 |

TABLE 17

Experimental conditions of pollen grain exposure to *R. novergicus* Wistar rats and their respective results. Saline solution subcutaneous injection (according control, 100 μL per animal), followed by a booster in the same conditions after 7 days. The chart shows the cell counts in pleural lavage 4 hours after the procedure (7 days after the booster, that is, on the 14$^{th}$ day) through intrapleural injection of 10 μg of pollen grains in a volume of 100 μL of saline solution per animal.

| N | CAM Leu tot | Mono % | Eos % | Neut % | Mono Millions | Eos Millions | Neut Millions |
|---|---|---|---|---|---|---|---|
| 1 | 29 | 67 | 33 | 0 | 6.6 | 3.3 | 0 |
| 2 | 53 | 24 | 5 | 71 | 3.9 | 0.8 | 11.7 |
| 3 | 39 | 63 | 36 | 1 | 7.4 | 4.2 | 0.1 |
| Average | | | | | 5.97 | 2.76 | 3.93 |
| Deviation | | | | | 1.8 | 1.75 | 6.70 |
| E.P.M. | | | | | 1.27 | 1.24 | 4.74 |

TABLE 18

Experimental conditions of pollen grain exposure to *R. novergicus* Wistar rats and their respective results. Subcutaneous injection of 50 μg of wild tobacco - WT - pollen grains (100 μL per animal, in saline solution), followed by a booster in the same conditions after 7 days. The chart shows the cell counts in pleural lavage 4 hours after the procedure (7 days after the booster, that is, on the 14$^{th}$ day) through intrapleural injection of 10 μg of pollen grains in a volume of 100 μL of saline solution per animal.

| N | CAM Leu tot | Mono % | Eos % | Neut % | Mono Millions | Eos Millions | Neut Millions |
|---|---|---|---|---|---|---|---|
| 1 | 31 | 51 | 35.5 | 13.5 | 6 | 4.2 | 1.6 |
| 2 | 24 | 80 | 17.5 | 2.5 | 6.1 | 1.3 | 0.2 |
| 3 | 29 | 63 | 30.5 | 6.5 | 5.5 | 2.7 | 0.6 |
| 4 | 26 | 50 | 46 | 4 | 3.9 | 3.3 | 0.6 |
| 5 | 28 | 82 | 14 | 4 | 7.3 | 1.3 | 0.4 |
| Average | | | | | 5.78 | 2.54 | 0.67 |
| Deviation | | | | | 1.25 | 1.26 | 0.54 |
| E.P.M. | | | | | 0.63 | 0.63 | 0.27 |

TABLE 19

Experimental conditions of pollen grain exposure to *R. novergicus* Wistar rats and their respective results. Subcutaneous injection of 500 μg of wild tobacco - WT - pollen grains (100 μL per animal, in saline solution), followed by a booster in the same conditions after 7 days. The chart shows the cell counts in pleural lavage 4 hours after the procedure (7 days after the booster, that is, on the 14$^{th}$ day) through intrapleural injection of 10 μg of pollen grains in a volume of 100 μL of saline solution per animal.

| N | CAM Leu tot | Mono % | Eos % | Neut % | Mono Millions | Eos Millions | Neut Millions |
|---|---|---|---|---|---|---|---|
| 1 | 48 | 49 | 6 | 45 | 8 | 0.98 | 7.34 |
| 2 | 47 | 53 | 10 | 37 | 8.97 | 1.69 | 6.26 |
| 3 | 61 | 76 | 5 | 19 | 14.8 | 0.98 | 3.71 |
| 4 | 33 | 89 | 10 | 1 | 8.8 | 0.99 | 0.10 |
| 5 | 41 | 62 | 3 | 35 | 8.6 | 0.42 | 4.88 |
| Average | | | | | 9.85 | 1.01 | 4.46 |
| Deviation | | | | | 2.81 | 0.45 | 2.80 |
| E.P.M. | | | | | 1.41 | 0.23 | 1.40 |

TABLE 20

Experimental conditions of pollen grain exposure to *R. novergicus* Wistar rats and their respective results. Subcutaneous injection of 50 μg of wild tobacco - WT - pollen grains (100 μL per animal, in saline solution with 5 mg of alumminum hydroxide as adjuvant), followed by a booster in the same conditions after 7 days. The chart shows the cell counts in pleural lavage 4 hours after the procedure (7 days after the booster, that is, on the 14$^{th}$ day) through intrapleural injection of 10 μg of pollen grains in a volume of 100 μL of saline solution per animal.

| N | CAM Leu tot | Mono % | Eos % | Neut % | Mono Millions | Eos Millions | Neut Millions |
|---|---|---|---|---|---|---|---|
| 1 | 49 | 77 | 8 | 15 | 13.58 | 1.41 | 2.65 |
| 2 | 23 | 76 | 17 | 7 | 5.94 | 1.33 | 0.55 |
| 3 | 49 | 73 | 13 | 14 | 11.09 | 1.97 | 2.13 |
| 4 | 33 | 82 | 15 | 3 | 8.12 | 1.49 | 0.30 |
| 5 | 56 | 56 | 15 | 29 | 9.41 | 2.52 | 4.87 |
| Average | | | | | 9.63 | 1.74 | 2.10 |
| Deviation | | | | | 2.90 | 0.50 | 1.85 |
| E.P.M. | | | | | 1.45 | 0.25 | 0.92 |

TABLE 21

Experimental conditions of pollen grain exposure to *R. novergicus* Wistar rats and their respective results. Subcutaneous injection of 500 μg of wild tobacco - WT - pollen grains (100 μL per animal, in saline solution with 5 mg of aluminum hydroxide as adjuvant), followed by a booster in the same conditions after 7 days. The chart shows the cell counts in pleural lavage 4 hours after the procedure (7 days after the booster, that is, on the 14$^{th}$ day) through intrapleural injection of 10 μg of pollen grains in a volume of 100 μL of saline solution per animal.

| N | CAM Leu tot | Mono % | Eos % | Neut % | Mono Millions | Eos Millions | Neut Millions |
|---|---|---|---|---|---|---|---|
| 1 | 47 | 67 | 2 | 31 | 11.34 | 0.34 | 5.25 |
| 2 | 94 | 62 | 5 | 33 | 22.15 | 1.79 | 11.79 |
| 3 | 32 | 68 | 3 | 29 | 6.96 | 0.31 | 3 |
| 4 | 56 | 69 | 4 | 27 | 12.36 | 0.72 | 4.84 |
| 5 | 52 | 71 | 18 | 11 | 11.08 | 2.81 | 1.72 |
| Average | | | | | 12.78 | 1.19 | 5.31 |
| Deviation | | | | | 5.63 | 1.08 | 3.89 |
| E.P.M. | | | | | 2.81 | 0.54 | 1.95 |

EXAMPLE 8

Immune Response of Rats Subjected to Subcutaneous Injection, Followed by a "Booster"—Challenge with 20 μg of Pollen Grains in the Pleural Cavity

TABLE 22

Experimental conditions of pollen grain exposure to *R. novergicus* Wistar rats and their respective results. Subcutaneous injection of saline solution (according to control 100 μL per animal), followed by a booster in the same conditions after 7 days. The chart shows the cell counts in pleural lavage of normal animals, which were not subjected to any program of sensitizing or challenge.

| N | CAM Leu tot | Mono % | Eos % | Neut % | Mono Millions | Eos Millions | Neut Millions |
|---|---|---|---|---|---|---|---|
| 1 | 15 | 89 | 11 | 0 | 4.3 | 0.5 | 0 |
| 2 | 25 | 84 | 16 | 0 | 6.3 | 1.2 | 0 |
| 3 | 14 | 71 | 25 | 4 | 3.2 | 1.1 | 0.2 |
| 4 | 21 | 88 | 12 | 0 | 5.9 | 0.8 | 0 |
| Average | | | | | 4.92 | 0.91 | 0.04 |
| Deviation | | | | | 1.45 | 0.31 | 0.09 |
| E.P.M. | | | | | 0.84 | 0.18 | 0.05 |

TABLE 23

Experimental conditions of pollen grain exposure to *R. novergicus* Wistar rats and their respective results. Subcutaneous injection of saline solution (according to control 100 μL per animal), followed by a booster in the same conditions after 7 days. The chart shows the cell counts in pleural lavage 4 hours after the procedure (7 days after the booster, that is, on the 14$^{th}$ day) through intrapleural injection of 20 μg of pollen in a volume of 100 μL of saline solution per animal.

| N | CAM Leu tot | Mono % | Eos % | Neut % | Mono Millions | Eos Millions | Neut Millions |
|---|---|---|---|---|---|---|---|
| 1 | 34 | 69 | 31 | 0 | 7.0 | 3.2 | 0 |
| 2 | 21 | 81 | 18 | 1 | 5.3 | 1.3 | 0.1 |
| 3 | 48 | 87 | 11 | 2 | 13.2 | 1.8 | 0.3 |
| 4 | 28 | 65 | 31 | 4 | 5.8 | 2.8 | 0.4 |
| 5 | 12 | 78 | 20 | 2 | 3 | 0.8 | 0.1 |
| Average | | | | | 6.88 | 1.98 | 0.16 |
| Deviation | | | | | 3.83 | 0.99 | 0.16 |
| E.P.M. | | | | | 1.92 | 0.50 | 0.08 |

TABLE 24

Experimental conditions of pollen grain exposure to *R. novergicus* Wistar rats and their respective results. Subcutaneous injection of 50 μg of wild tobacco pollen grains (100 μL per animal, in a saline solution with 5 mg of aluminum hydroxide as adjuvant), followed by a booster in the same conditions after 7 days. The chart shows the cell counts in pleural lavage 4 hours after the procedure through intrapleural injection of 20 μg of pollen grains in a volume of 100 μL of saline solution per animal.

| N | CAM Leu tot | Mono % | Eos % | Neut % | Mono Millions | Eos Millions | Neut Millions |
|---|---|---|---|---|---|---|---|
| 1 | 22 | 78 | 21 | 1 | 5.5 | 1.5 | 0.1 |
| 2 | 40 | 71.5 | 26.5 | 2 | 8.6 | 3.2 | 0.2 |
| 3 | 16 | 78 | 21 | 1 | 4.2 | 1.1 | 0.1 |
| 4 | 19 | 88 | 12 | 0 | 5.7 | 0.8 | 0 |
| 5 | 19 | 81 | 10 | 9 | 5.2 | 0.6 | 0.6 |
| 6 | 24 | 75 | 17 | 8 | 5.9 | 1.3 | 0.6 |
| Average | | | | | 12.96 | 1.43 | 0.26 |
| Deviation | | | | | 6.17 | 0.92 | 0.28 |
| E.P.M. | | | | | 2.76 | 0.41 | 0.12 |

TABLE 25

Experimental conditions of pollen grain exposure to *R. novergicus* Wistar rats and their respective results. Subcutaneous injection of 100 μg of wild tobacco pollen grains (100 μL per animal, in saline solution with 5 mg of aluminum hydroxide as adjuvant), followed by a booster in the same conditions after 7 days. The chart shows the cell counts in pleural lavage 4 hours after the procedure through intrapleural injection of 20 μg of pollen grains in a volume of 100 μL of saline solution per animal.

| N | CAM Leu tot | Mono % | Eos % | Neut % | Mono Millions | Eos Millions | Neut Millions |
|---|---|---|---|---|---|---|---|
| 1 | 32 | 81 | 16 | 3 | 8.81 | 1.74 | 0.33 |
| 2 | 15 | 80.5 | 19 | 0.5 | 4.11 | 0.97 | 0.03 |
| 3 | 19 | 84 | 15 | 1 | 5.11 | 0.91 | 0.06 |
| 4 | 27 | 69 | 27 | 4 | 5.96 | 2.33 | 0.35 |
| 5 | 23.25 | 78 | 22 | 0 | 6.89 | 1.9 | 0 |
| 6 | 23.25 | 80 | 9 | 11 | 6.32 | 0.7 | 0.87 |
| Average | | | | | 6.20 | 1.43 | 0.27 |
| Deviation | | | | | 1.61 | 0.66 | 0.33 |
| E.P.M. | | | | | 0.72 | 0.29 | 0.15 |

EXAMPLE 9

Immune Response of Rats Subjected to Subcutaneous Injection of Pollen Grains, Followed by a Booster—Challenge Through Subplantar Injection of 20 μg of Pollen Grains Two groups of animals were subjected to a subcutaneous injection (100 µL per animal) of pollen grain suspensions in the following conditions:
1—Subcutaneous injection of 50 µg of pollen grains in a saline solution and aluminum hydroxide as adjuvant (5 mg per animal); and 2—Subcutaneous injection of 100 µg of pollen grains in a saline solution and aluminum hydroxide as adjuvant (5 mg per animal).

One week after these subcutaneous injections (day 7) the groups of animals were subjected to a new subcutaneous injection (booster) in the same respective pollen grain concentrations, but without an adjuvant. After one week (day 14), all animal groups were challenged by sub plantar injection (50 µL) of 20 µg suspensions of pollen grains. There was no appearance of edemas on the sole of the paws/feet in any of the evaluated conditions.

EXAMPLE 10

Immune Response of Rats Subjected to Intranasal Instillation of Pollen Grains, Followed by a Booster—Challenge Through Subplantar Injection of 20 µg of Pollen Grains Four groups of animals were subjected to an intranasal instillation (50 µL per nostril) of pollen grain suspensions under the following conditions:
1—Intranasal instillation of 50 µg of pollen grains in saline solution;
2—Intranasal instillation of 25 µg of pollen grains in saline solution;
3—Intranasal instillation of 50 µg of pollen grains in saline solution and aluminum hydroxide as adjuvant (5 mg per animal); and
4—Intranasal instillation of 25 µg of pollen grains in saline solution and aluminum hydroxide as adjuvant (5 mg per animal).

One week after these nasal instillations (day 7) the animal groups were subjected to another intranasal administration (booster) with the same respective concentrations of pollen grains, but without adjuvants. After one week (day 14), all animal groups were challenged by a sub plantar injection (50 µL) of suspensions of 20 µg of pollen grains. There was no occurrence of paw/feet edemas in any of the evaluated conditions.

EXAMPLE 11

Immune Response of Rats Subjected to Consecutive Intranasal Instillations with WT and GM Tobacco Pollen Grains Groups of animals were subjected to intranasal instillations (50 µL per nostril) of wild pollen (WT) suspensions or transgenic pollen suspensions (GM—whose pollen grains contain the GUS protein) in the concentrations of 0, 5 and 50 total pollen µg per animal. Three instillations were performed with intervals of 7 days, after which a broncho-alveolar washing as well as a cellular counting was performed

TABLE 26

Experimental conditions of pollen grain exposure to *R. novergicus* Wistar rats and their respective results. Nasal instillation of a saline solution (control of 50 µL per nostril, per animal) in three consecutive exposures with intervals of one week between each exposure. The chart presents the cell counts in lavage broncho-alveolar 4 hours after the last instillation under the above-described conditions.

| N | CAM Leu tot | Mono % | Eos % | Neut % | Mono Millions | Eos Millions | Neut Millions |
|---|---|---|---|---|---|---|---|
| 1 | 7 | 70 | 0 | 30 | 0.123 | 0 | 0.053 |
| 2 | 6 | 96 | 0 | 4 | 0.144 | 0 | 0.006 |
| 3 | 10 | 60 | 0 | 40 | 0.15 | 0 | 0.1 |

TABLE 26-continued

Experimental conditions of pollen grain exposure to *R. novergicus* Wistar rats and their respective results. Nasal instillation of a saline solution (control of 50 µL per nostril, per animal) in three consecutive exposures with intervals of one week between each exposure. The chart presents the cell counts in lavage broncho-alveolar 4 hours after the last instillation under the above-described conditions.

| N | CAM Leu tot | Mono % | Eos % | Neut % | Mono Millions | Eos Millions | Neut Millions |
|---|---|---|---|---|---|---|---|
| Average | | | | | 0.138 | 0 | 0.053 |
| Deviation | | | | | 0.014 | 0 | 0.047 |
| E.P.M. | | | | | 0.01 | 0 | 0.033 |

TABLE 27

Experimental conditions of pollen grain exposure to *R. novergicus* Wistar rats and their respective results. Nasal instillation of 5 µg of wild tobacco pollen grains - WT - (in a saline solution, instillation of 50 µL per nostril, per animal) in three consecutive exposures with intervals of one week between each exposure. The chart presents the cell counts in lavage broncho-alveolar 4 hours after the last instillation under the above-described conditions.

| N | CAM Leu tot | Mono % | Eos % | Neut % | Mono Millions | Eos Millions | Neut Millions |
|---|---|---|---|---|---|---|---|
| 1 | 54 | 51 | 0 | 49 | 0.689 | 0 | 0.662 |
| 2 | 50 | 48 | 0 | 52 | 0.6 | 0 | 0.65 |
| 3 | 27 | 55 | 0 | 45 | 0.371 | 0 | 0.304 |
| 4 | 28 | 43 | 0 | 57 | 0.301 | 0 | 0.399 |
| Average | | | | | 0.49 | 0 | 0.503 |
| Deviation | | | | | 0.184 | 0 | 0.18 |
| E.P.M. | | | | | 0.106 | 0 | 0.104 |

TABLE 28

Experimental conditions of pollen grain exposure to *R. novergicus* Wistar rats and their respective results. Nasal instillation of 5 µg of transgenic tobacco pollen grains - GM - (in a saline solution, instillation of 50 µL per nostril, per animal) in three consecutive exposures with intervals of one week between each exposure. The chart presents the cell counts in lavage broncho-alveolar 4 hours after the last instillation under the above-described conditions.

| N | CAM Leu tot | Mono % | Eos % | Neut % | Mono Millions | Eos Millions | Neut Millions |
|---|---|---|---|---|---|---|---|
| 1 | 48 | 30 | 0 | 70 | 0.36 | 0 | 0.84 |
| 2 | 29 | 58 | 0 | 42 | 0.421 | 0 | 0.305 |
| 3 | 75 | 37 | 1 | 62 | 0.694 | 0.019 | 1.163 |
| 4 | 39 | 63 | 0 | 37 | 0.614 | 0 | 0.361 |
| Average | | | | | 0.522 | 0.005 | 0.667 |
| Deviation | | | | | 0.157 | 0.009 | 0.408 |
| E.P.M. | | | | | 0.091 | 0.005 | 0.236 |

TABLE 29

Experimental conditions of pollen grain exposure to *R. novergicus* Wistar rats and their respective results. Nasal instillation of 50 µg of wild tobacco pollen grains - WT - (in a saline solution, instillation of 50 µL per nostril, per animal) in three consecutive exposures with intervals of one week between each exposure. The chart presents the cell counts in lavage broncho-alveolar 4 hours after the last instillation under the above-described conditions.

| N | CAM Leu tot | Mono % | Eos % | Neut % | Mono Millions | Eos Millions | Neut Millions |
|---|---|---|---|---|---|---|---|
| 1 | 172 | 4 | 0 | 96 | 0.172 | 0 | 4.128 |
| 2 | 24 | 51 | 0 | 49 | 0.306 | 0 | 0.294 |
| 3 | 109 | 20 | 0 | 80 | 0.545 | 0 | 2.180 |

TABLE 29-continued

Experimental conditions of pollen grain exposure to *R. novergicus* Wistar rats and their respective results. Nasal instillation of 50 μg of wild tobacco pollen grains - WT - (in a saline solution, instillation of 50 μL per nostril, per animal) in three consecutive exposures with intervals of one week between each exposure. The chart presents the cell counts in lavage broncho-alveolar 4 hours after the last instillation under the above-described conditions.

| N | CAM Leu tot | Mono % | Eos % | Neut % | Mono Millions | Eos Millions | Neut Millions |
|---|---|---|---|---|---|---|---|
| 4 | 39 | 66 | 0 | 34 | 0.644 | 0 | 0.332 |
| 5 | 104 | 56 | 0 | 44 | 1.456 | 0 | 1.144 |
| Average | | | | | 0.624 | 0 | 1.615 |
| Deviation | | | | | 0.216 | 0 | 1.6 |
| E.P.M. | | | | | 0.25 | 0 | 0.8 |

TABLE 30

Experimental conditions of pollen grain exposure to *R. novergicus* Wistar rats and their respective results. Nasal instillation of 50 μg of transgenic tobacco pollen grains - GM - (in a saline solution, instillation of 50 μL per nostril, per animal) in three consecutive exposures with intervals of one week between each exposure. The chart presents the cell counts in lavage broncho-alveolar 4 hours after the last instillation under the above-described conditions.

| N | CAM Leu tot | Mono % | Eos % | Neut % | Mono Millions | Eos Millions | Neut Millions |
|---|---|---|---|---|---|---|---|
| 1 | 31 | 92 | 0 | 8 | 0.713 | 0 | 0.062 |
| 2 | 65 | 70 | 0 | 30 | 1.138 | 0 | 0.488 |
| 3 | 22 | 44 | 3 | 53 | 0.242 | 0.02 | 0.292 |
| 4 | 40 | 48 | 0 | 52 | 0.480 | 0 | 0.52 |
| 5 | 35 | 55 | 0 | 45 | 0.481 | 0 | 0.394 |
| Average | | | | | 0.610 | 0.003 | 0.351 |
| Deviation | | | | | 0.338 | 0.007 | 0.184 |
| E.P.M. | | | | | 0.169 | 0.004 | 0.092 |

The results of tables 26-30 are better visualized in FIG. 3, panels D-F, and indicate that in none of the pollen grain concentrations administered by intranasal means any significant alteration in the cell counts (which would be typical of allergic-inflammatory reactions) occurred. The statistically significant difference among the mononuclear cells and neutrophil counts after the administration of pollen grains WT and GM (FIG. 3, panels D and E) is surprising and favorable in regard to the present invention's purposes, since it demonstrates that the pollen grains with modified composition (GM), when used in concentrations of 50 μg, would have less potential to induce inflammation in the broncho-alveolar cavity than wild tobacco pollen grains (WT).

EXAMPLE 12

Immune Response of Rats Subjected to Different Programs of Pollen Grain Administration—Measurement of the Total Seric IgG Through ELISA Table 31 shows the seric IgG concentration data of the animals subjected to the conditions described in Example 6, tables 12-15.

TABLE 31

Concentration data of the total seric IgG, in μg/mL, in serum samples of animals subjected to three consecutive intranasal administrations, with an interval of one week between each application of wild type tobacco pollen grain (WT) suspensions in different concentrations.

| Animal | Saline solution | WT 5 μg | WT 50 μg | WT 500 μg |
|---|---|---|---|---|
| 1 | 1125.6 | 1441.5 | 1123.3 | 1012.7 |
| 2 | 1367 | 1337.7 | 1459.5 | 1461.8 |
| 3 | 1376 | 1084.9 | 1414.4 | 1152.6 |
| 4 | 1545.3 | 836.7 | 1511.4 | 918 |
| 5 | 1504.6 | | | 1015 |
| 6 | | | | 1488.9 |
| N | 5 | 4 | 4 | 6 |
| Average | 1383.7 | 1175.2 | 1377.2 | 1174.8 |
| Deviation | 164.1 | 270.8 | 173.8 | 244.7 |
| E.P.M. | 82.0 | 156.4 | 100.4 | 109.4 |

Table 32 shows the seric IgG concentration data of the animals subjected to the conditions described in Example 7, tables 16 and 19-21.

TABLE 32

Concentration data of the total seric IgG, in μg/mL, in serum samples of animals subjected to an intrapleural injection with different concentrations of wild type tobacco pollen grains (WT), with or without adjuvant (AlOH$_3$), followed by a booster one week later, under the same conditions and challenge, and, one week thereafter by an intrapleural injection of 10 μg of pollen grains.

| Animal | Saline solution | 500 μg | 50 μg + AlOH$_3$ | 500 μg + AlOH$_3$ |
|---|---|---|---|---|
| 1 | 942.8 | 956.3 | 981.1 | 951.8 |
| 2 | 807.4 | 665.2 | 906.7 | 1037.5 |
| 3 | 1024 | 836.7 | 678.8 | 1367 |
| 4 | 784.8 | 884.1 | 1100.7 | 960.8 |
| 5 | | | 954.1 | 1673.9 |
| N | 4 | 4 | 5 | 5 |
| Average | 889.8 | 835.6 | 924.3 | 1198.2 |
| Deviation | 113.5 | 123.8 | 154.8 | 315.3 |
| E.P.M. | 65.5 | 71.5 | 77.4 | 157.7 |

Table 33 shows the seric IgG concentration data of the animals subjected to the conditions described in Example 11, tables 26-30.

TABLE 33

Concentration data of the total seric IgG, in μg/mL, in serum samples of animals subjected to 3 (three) consecutive intranasal administrations, with an interval of one week between each application of wild type tobacco pollen grain (WT) suspensions or genetically modified (GM) in different concentrations.

| Animal | Saline solution | WT 5 μg | WT 50 μg | GM 5 μg | GM 50 μg |
|---|---|---|---|---|---|
| 1 | | 1098.5 | 1069.1 | 967.6 | 523.1 |
| 2 | 1130.1 | 1457.3 | 1247.4 | 1062.4 | 784.8 |
| 3 | 1470.8 | 1078.2 | 931.5 | 1299.3 | 978.9 |
| 4 | 1283.5 | 1367 | 958.6 | 1048.8 | 893.1 |
| 5 | 1479.8 | 723.9 | 1103 | | 744.2 |
| N | 4 | 5 | 5 | 4 | 5 |
| Average | 1341.1 | 1145.0 | 1061.9 | 1094.5 | 784.8 |
| Deviation | 167.2 | 287.6 | 126.3 | 142.8 | 172.9 |
| E.P.M. | 96.6 | 143.8 | 63.2 | 82.4 | 86.4 |

EXAMPLE 13

Analysis of the Immune Response of Rats Subjected to Consecutive Subcutaneous Injections of Pollen Grains, Recognized as Allergens (*Betula fontinallis*)

Aiming to subject the animals to conditions in which an inflammatory and/or allergic response would be more likely, so as to eliminate the hypothesis that the animals utilized in the tests would not be responsive, new trials were conceived with the use of pollen grains reported in literature to be associated with allergic events (Ahlholm et al, "Genetic and Environmental Factors Affecting the Allergenicity of Birch (*Betula pubescens* ssp. czerepanovii [Orl.] Hamet-ahti) Pollen" Clin. Exp. Allergy 28:1384-1388, 1998). In this sense, the pollen grains of *Betula fontinallis* were commercially acquired and utilized in experiments with rats as follows:

Groups of 5 (five) animals were subjected to the exposure of pollen grains in the following conditions:
Group 1—Subcutaneous Injection (100 µL Per Animal):
  *Betula* pollen suspension (100 µg/animal) in saline solution;
  *Betula* pollen suspension (100 µg/animal) in saline solution+Al(OH)$_3$ (5 mg/animal); and
  Wild tobacco pollen suspension—WT (100 µg/animal) in saline solution+Al(OH)$_3$ (5 mg/animal).
Group 2—Instillation (50 µL Per Nostril):
  *Betula* pollen suspension (100 µg/animal) in saline solution+Al(OH)$_3$ (5 mg/animal).

After eight (8) weeks of consecutive exposures under the above-described conditions, Group 1 was subjected to a challenge, by injection into the footpad, of 50 µg of pollen grain suspension (50 µL) and measurement of the animal's feet volume in a plethysmograph. The results of Table 34 indicate the occurrence of edemas in the animals subjected to subcutaneous injections of WT tobacco pollen and, to a lesser degree, with *Betula* pollen.

TABLE 34

The volumes, in ml, of the right (control) and the left paws/feet (challenge) were measured in a plethysmograph. The rats were subjected to 8 (eight) consecutive subcutaneous injections with pollen grains under the above-described conditions, followed by a challenge through a sub plantar injection of 50 µg of pollen grain suspension (50 µL per paw). The presented averages represent the volume differences between the left and right paws.

| Tobacco WT + Al(OH)$_3$ | | *Betula* in saline solution | | *Betula* + Al(OH)$_3$ | |
| --- | --- | --- | --- | --- | --- |
| Right | Left | Right | Left | Right | Left |
| 1.23 | 1.79 | 1.29 | 1.54 | 1.24 | 1.36 |
| 1.23 | 1.80 | 1.35 | 1.58 | 1.38 | 1.28 |
| 1.30 | 1.75 | 1.28 | 1.48 | 1.31 | 1.34 |
| 1.20 | 1.30 | | | 1.40 | 1.42 |
| | | | | 1.32 | 1.29 |
| Average | 0.420 | | 0.227 | | 0.008 |
| Deviation E.P.M. | 0.220 | | 0.025 | | 0.081 |

After eight consecutive weeks of nasal instillations in the animals of Group 2, broncho-alveolar lavages were used to count the cells under the above-described conditions. The cell counts indicated that there was no change in relation to the control animals. Taken together these results point to the following conclusions: (i) the allergic response to subcutaneously injected pollen grains only occurs after an elevated number of consecutive exposures and tends to be higher in the absence of an adjuvant; (ii) it was not possible to detect typical alterations of allergic responses in any of the nasal instillation conditions in rats. Since edemas indeed occurred under the subcutaneous injection condition (with WT tobacco pollen and also with *Betula* pollen) and the absence of typical allergic alterations through instillation in all of the conditions evaluated in the present invention, the results indicate that there seems to be a relation between the antigen presentation route and the pattern of response.

EXAMPLE 14

Immune Response of Rats Subjected to Different Programs of Pollen Grains Administration—Detection of Specific Seric IgG Against of Pollen Grain Proteins Through Western Blot The formation of specific seric IgG against pollen grain proteins was monitored through Western Blot, in which total extracts of pollen WT (wild) and GM (containing the GUS enzyme) proteins were separated through electrophoresis, followed by the transference of the bands to a nitrocellulose membrane. The serum of the animals subjected to three consecutive instillations, in intervals of one week each, with pollen WT or GM, in pool, were then incubated separately, with said membrane (previously cut into pieces to allow the separation of the samples), which, after being washed, was incubated in the presence of secondary anti-rat IgG antibodies marked with alkaline phosphatase. The colorimetrical reaction with adequate substrates indicated the detection of specific IgG's against pollen grain proteins. As shown on Table 35, the serum of the animals instilled with tobacco pollen grains "WT" and also in the serum of the animals instilled with tobacco pollen grains "GM" revealed the presence of IgG type antibodies specific against proteins of said pollen grains. Taken together, the results of these experiments point to the feasibility of the use of pollen grains as modulators of the immune response in mammals. More specifically, the results point to the feasibility of the use of whole pollen grains as stimulators of protective response (formation of specific seric IgG against pollen grain proteins) in mammals.

TABLE 35

Detection, through Western Blot, of specific seric IgG against proteins from tobacco pollen grains WT and GM.

| | Condition of exposure | | | |
| --- | --- | --- | --- | --- |
| | Saline solution | Pollen WT 5 µg | Pollen GM 5 µg | Pollen GM 50 µg |
| seric IgG | − | + | + | − |

The approach using pollen grains has, besides other advantages mentioned in the present invention, the important characteristic of requiring very small amounts of vegetal material for immunization. The results of Table 35 show the formation of specific seric IgG against proteins present in pollen grains after three (3) administrations of 5 µg of pollen grains. Even though no study was so far performed in order to define the minimum amounts necessary to induce the immune response observed on Table 35, the present results offer a reasonable base to estimate the amount of pollen grains that would be necessary for the immunization in other species, such as humans. It is known that the human immune system is considered to be from 100 to 1.000 times more sensitive than that of murines, which means that, by maintaining the proportion between the administered amount and the body weight, just some dozens or hundreds of square meters of cultivation would be sufficient to produce vaccines for entire populations. This allows, among other things, the adoption of simple containment measures in order to decrease biosafety concerns. Further, it is convenient to remember that several other strategies for pollen grain containment are available, such as irradiation, the use of suicidal genes, and infertility barriers. The present invention's strategy is particularly applicable for animal vaccinations, being also useful to fight epidemics and prevent or remedy situations which might result from the use of biological weapons or terrorist attacks.

EXAMPLE 15

Obtaining Genetic Constructions for the Transformation of Plants Destined to Produce Pollen Grains with Heterologous Polypeptides on their External Surface In another preferred embodiment of the present invention, the presence of heterologous polypeptides on the external surface of pollen grains is desirable because it is related to the use of pollen grains in in vitro antigen-antibody type reactions, that is, reactions used for in vitro immune diagnosis. In order to evaluate this applicability, A. thaliana plants were transformed with gene constructions which would direct the expression of heterologous polypeptide in a subcellular localization compatible with its presence on the external surface of the pollen grains.

Figure 5:
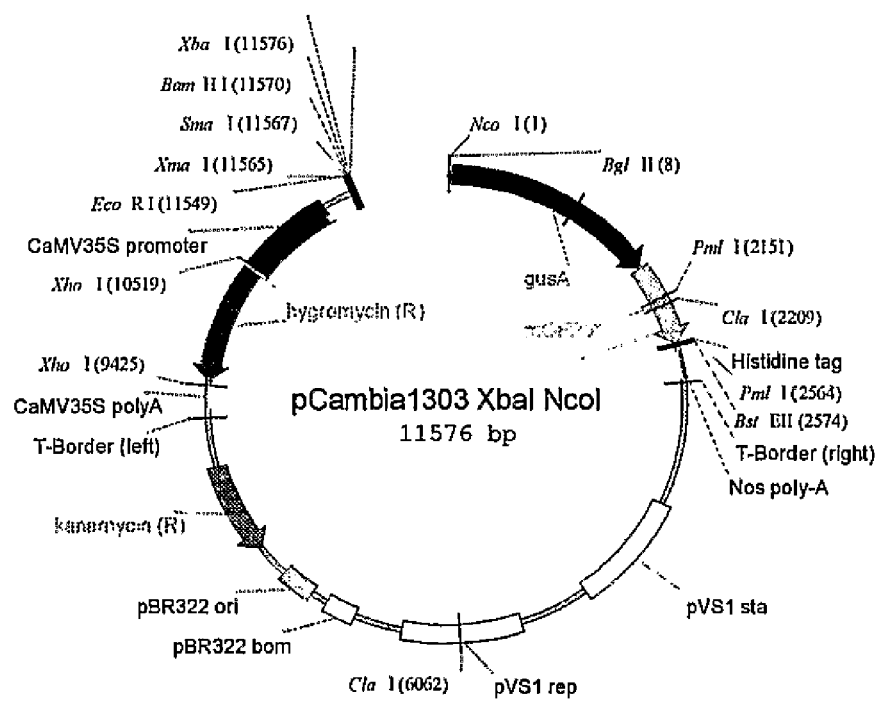
FIG. 5 is a schematic representation of the binary plasmid pCambia 1303 without the CaMV 35S promoter region, as per the cleavage with XbaI and NcoI enzymes.
Figure 7:
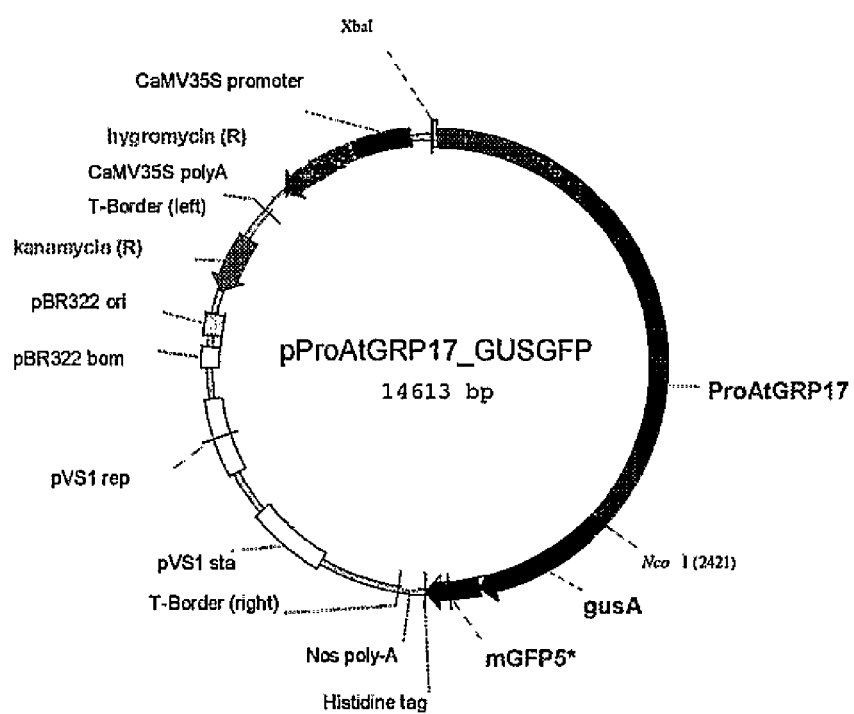
FIG. 7 is a schematic representation of the plasmid pProAtGRP17_GUSGFP, resulting from the cloning of the PCR product ProAtGRP67 cleaved with XbaI and NcoI in the plasmid pCAMBIA 1303 cleaved with the same enzymes. The 616 bp region corresponding to the part of the AtGRP17 promoter region and the AtGRP17 gene ORF are indicated as ProArGRP17. Reporter genes GUS and GFP are also indicated.

In order to fulfill these requirements, in one of the preferred embodiments of the present invention, the coding gene of the heterologous polypeptide promoter SEQ ID NO. 2) in question is translationally fused to the coding sequence of the AtGRP17 gene (SEQ ID NO. 1), while said fusion is controlled by at least part of the promoter region (SEQ ID NO. 3) of the AtGRP17, this promoter being able to direct the gene fusion expression in the anther's tapetum. In order to prepare said gene construction, the following steps were taken:

For the amplification of the promoter region of the AtGRP17 and its ORF specific oligonucleotides were used: RR1f (5'ATA AAG CTT TTT CTC TGT TTT TGT CCG TGG AAC) (SEQ. ID NO. 4) and RR2r (5'ATA CCA TGG CAC GTG ATT CGG TGG AAG TCC TGC C) (SEQ. ID NO. 5). The plasmid pC027 (described by Olivera et al "Inflorescence-specific genes from Arabidopsis thaliana encoding glycine-rich proteins". Plant J. 3: 495-507, 1993; Franco et al., "Distal regulatory regions restrict the expression of cis-linked gene to the tapetal cells". FEBS Letters 25965: 1-6, 2002) was used as target for the amplification, by PCR, of the promoter region and of the AtGRP17 ORF. By using the oligonucleotides RR1f and RR2r the product of amplification ProAtGRP67 (FIG. 6) was obtained and, after cleavage with the enzymes XbaI and NcoI, was linked to plasmid pCambia cleaved with the same enzymes (FIG. 5), thus originating the construction pProAtGRP17_GUSGFP (FIG. 7).

EXAMPLE 16

Transformation of A. thaliana and Analysis of the Heterologous Polypeptide's Localization The gene construction of the previous example was introduced in E. coli and in Agrobacterium tumefaciens so as to later transform A. thaliana. Plant transformation confirmation was performed through the extraction of genomic DNA by methodologies known to skilled in the art and by PCR-mediated amplification of the heterologous regions introduced into the transformed plant. Plant transformation was also confirmed by the expression analysis of GUS enzyme activity in the intended subcellular localizations, by means of a calorimetric reaction using X-Gluc as substrate and the corresponding blue color formation. Plant tissue samples were observed by stereoscopic and optical microscopy.

Figure 8:
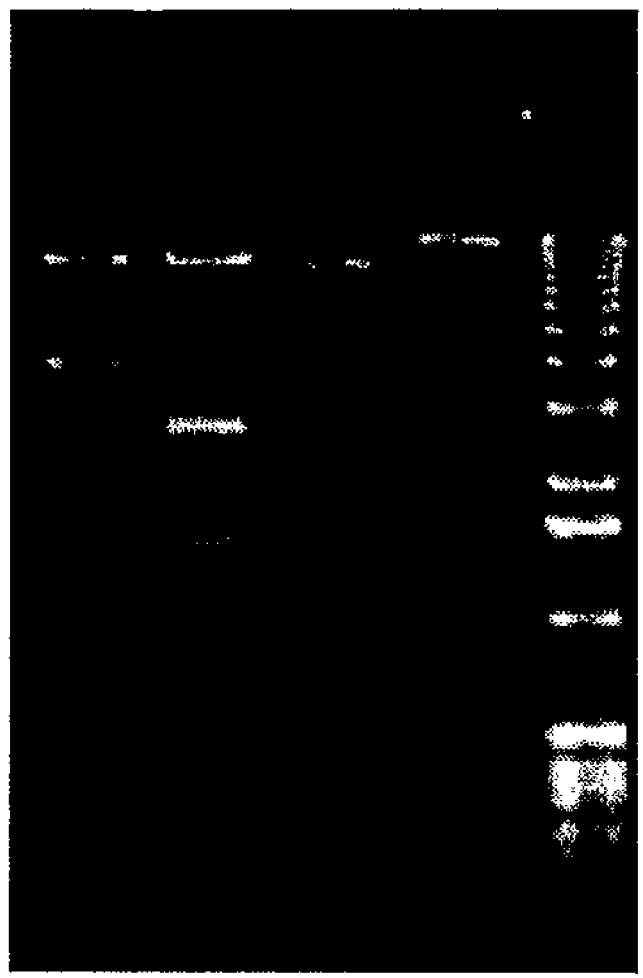
FIG. 8 shows 1% agarose gel containing the expected DNA fragments of the plasmids extracted from transformed *E. coli* XL1, obtained after cleavage with the indicated enzymes. 1, pCambiaProAtGRP17 PvuII; 2, pCambiaProAtGRP17 BglII; 3, pCambia PvuII; 4, pCambia BglII; 5, 1 kb ladder marker.
Figure 9:
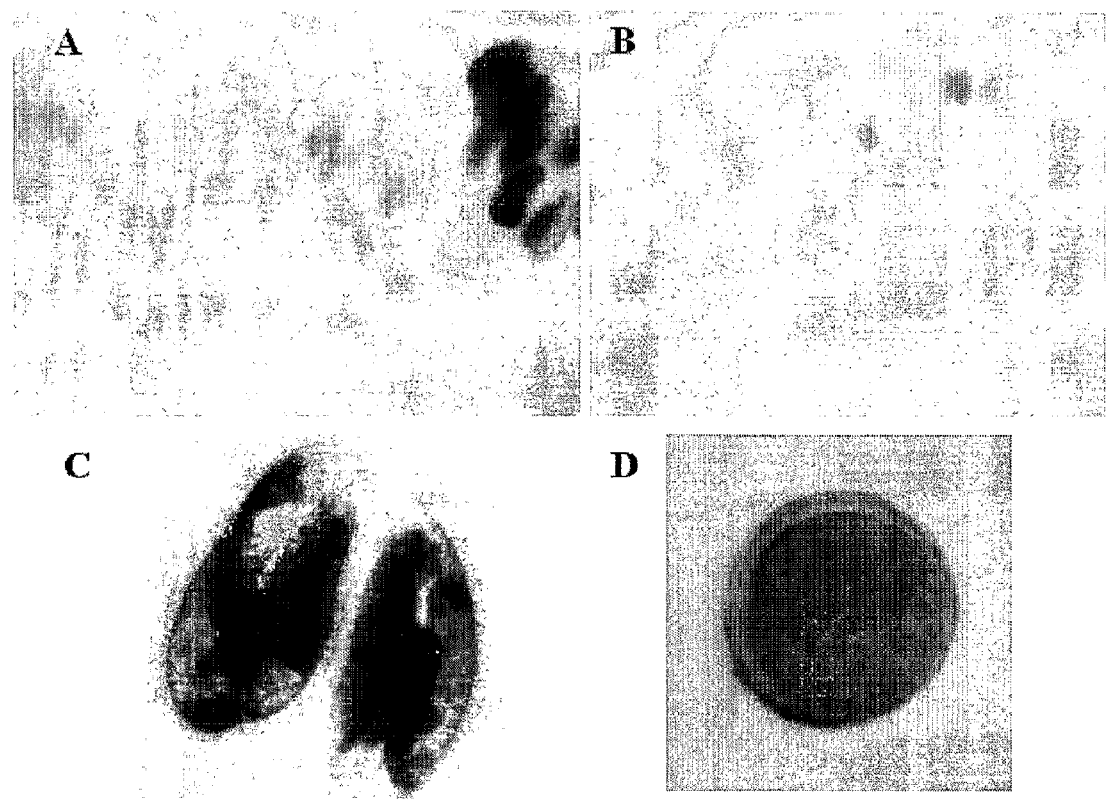
FIG. 9 shows floral structures of *A. thaliana* transformed with the plasmid pCambiaProAtGRP17GUSGFP. Panel A) shows the presence and activity of GUS on the late anthers' development, but not in the initial stages of development. Panel B) shows inflorescences of the same plant in which the activity of GUS can be seen in the anthers of immature flowers (left) and in the anthers and petals of the mature flower (right). Panel C) shows intense GUS activity on the tapetum and on the pollen grains. Panel D) shows a pollen grain with positive stain for GUS. All photographs were taken under an optical microscope.

The gene construction (FIG. 7) containing the reporter genes gus and gfp, was introduced in E. coli by electroporation and in A. tumefaciens by thermal shock. The cloning was confirmed by the analysis of the expected profile of fragments generated by the digestion with restriction enzymes (FIG. 8). A. thaliana inflorescences were inoculated with cultures of A. tumefaciens containing said gene construction (transformation technique called "floral dip", described by Clough & Bent "Floral dip: a Simplified Method for Agrobacterium-mediated Transformation of Arabidopsis thaliana" The Plant Journal 16(6):735-743, 1998). The seeds generated after that procedure were collected and sown on plaques containing a selective medium comprising hygromicyn. The plantlets selected from the plaques were transplanted into the soil in phytothron, where they were cultivated in conditions which favor self-fertilization. Analysis of these plants' inflorescences by microscopy (FIG. 9 A-D) confirmed the presence of GUS activity in the expected subcellular localization (by means of the corresponding colorimetrical reaction described in Example 2). More specifically, the activity of the GUS enzyme was only detected in the later stages of the anther's development (FIG. 9 A), and still more specifically on the anther's tapetum (FIG. 9 C).

EXAMPLE 17

Detection of the Heterologous Polypeptide on the Surface of Pollen Grains

The transformation of A. thaliana plants according to Example 16 resulted in the generation of 11 lineages effectively producing heterologous polypeptides in the pollen grains. Those lineages were cultivated in phytotron and self-pollinated so as to allow the later obtention of hundreds of seeds. Seeds of each one of the lineages were sown directly into the soil and the resulting plants were cultivated in phytotron. After inflorescence formation entire flowers were collected in Eppendorf tubes with the help of a scalpel. 100 μL of phosphate buffer 0.1 M pH 7 was added to said tubes, which were then vortexed in order to allow the formation of homogeneous pollen grain suspensions. Afterwards, 1 μL of the X Gluc reagent was added and, 30 minutes at 37° C. thereafter, the presence of the GUS enzyme triggered the formation a blue-colored complex. Fractions of these suspensions were then collected with micropipette and put on glass slides for observation under the microscope. The result of that observation (FIG. 9 D) indicated the presence of the active heterologous polypeptide (GUS enzyme) in the pollen grain. These results point collectively to the feasibility of the use of whole pollen grains as reagents for immune diagnosis.

The skilled persons will understand from the present description that any heterologous polypeptide can be produced by the processes of the present invention, including post-translationally modified polypeptides, such as glycosylated proteins and the like. Similarly, combinations of heterologous polypeptides or translational fusions of heterologous polypeptide segments may be produced by the teachings of the present invention, including, but not limiting to, at least part of polypeptides derived from eukaryotic organisms such as mammals including humans, plants, parasites, fungi or derived from procaryotic organisms such as bacteria or even viruses, as well as combinations thereof, regardless of being natural or synthetic polypeptides. Therapeutic peptides preferred for the purposes of the present invention include peptidic hormones, cytokines, interleucins, antibodies (and/or fragments thereof) and combinations thereof. The heterologous polypeptides produced by these processes may be used in several immunoreactions, including the immunomodulation of mammals and in vitro immunodiagnostic reactions.

The referred immunomodulation may have an immunotherapic, immunoprotective or vaccination purpose, according to the chosen immunogen and/or according the combination of the chosen immunogens.

The invention claimed is:

1. A pharmaceutical product for vaccination of vertebrates, the pharmaceutical product comprising genetically modified pollen grains, the pollen grains comprising:

a) a promoter consisting of nucleotides 954 to 1569 of the promoter sequence SEQ ID NO. 2 operably linked to the coding sequence SEQ ID NO. 1, whereby the coding sequence SEQ ID NO. 1 is under control of the last 616 bp of the promoter sequence SEQ ID NO. 2;

b) the coding sequence SEQ ID NO. 1 being fused in-frame to a coding sequence for a heterologous polypeptide, wherein both the promoter sequence and the coding sequence are present in the genome of the pollen grains; and c) the polypeptide of sequence SEQ ID NO. 3 translationally fused to the heterologous polypeptide, the heterologous polypeptide being present in the outer surface of the pollen grain.

2. The pharmaceutical product according to claim 1, wherein the heterologous polypeptide is selected from the group consisting of eukaryotic antigens, prokaryotic antigens, viral antigens, synthetic antigens, therapeutic peptides, peptidic hormones, cytokines, interleukins, and combinations thereof.

* * * * *

SEQUENCE LISTING

<160> NUMBER OF SEQ ID NOS: 5

<210> SEQ ID NO 1
<211> LENGTH: 1818
<212> TYPE: DNA
<213> ORGANISM: Arabidopsis thaliana

<400> SEQUENCE: 1

```
atgagcgaag aactaagtca aaagccatca tcagctcagt ctctgtcact gagagagggc      60
agaaataggt ttccttttct gtccctgtca cagagagagg gcagattttt tccttctcta     120
tctctttcag agagagatgg aagaaagttt tcttttctca gtatgttctc ttttctcatg     180
ccactgttgg aggttattaa gattattatt gcttctgtgg cctccgtaat cttcgtcggt     240
ttcgcctgtg taaccctcgc tggttctgcc gcagcattag tcgtaagcac cccggttttc     300
atcatattta gtcctgttct cgtaccagct acgatagcca cggttgtctt ggcgacagga     360
ttcacggccg gtggctcttt tggagcgacg gcacttggtc tcatcatgtg gcttgttaag     420
taagattatt ataacagctt atattgagat cactcgagat ttatgcttaa ttatataata     480
ttcataaacc tatagtttaa aagtatattg aacttcattt gttaacgtac tttataaata     540
ttgaacttcg ttcgttttct taattggtct ctaagtatat atacatactt ttttgtgtga     600
tgcagacgta ggatgggagt aaagccgaag gataatccac ctccggcagg acttccaccg     660
aattcgggag caggagcagg aggagctcaa agtctgatca aaaagtcaaa ggcaaagtct     720
aaaggtgggc ttaaggcttg gtgtaagaag atgttaaaaa gtaaattcgg tggtaaaaaa     780
ggcaagtccg ggggtggaaa aagtaaattt ggaggtaaag gcggtaagtc cgaaggtgaa     840
gaaggtatgt cgtctgggga tgaaggtatg tctggaagtg aaggaggtat gtccggaggt     900
gaaggaggta aatccaaaag tggaaaaggt aaactcaaag ctaaactcga aagaaaaaa     960
ggtatgtccg gagggtccga gagtgaagaa ggtatgtctg gaagtgaagg aggtatgtct    1020
ggtggtggag gaagtaaatc caaaagtaaa aaaagtaaac tcaaagctaa attgggaaag    1080
aaaaaaggta tgtccggagg catgtcagga agtgaagaag gtatgtctgg aagtgaagga    1140
ggtatgtcca gtggtggagg aagtaaatcc aaaagtaaaa aaagtaaact caaagctaaa    1200
ttgggaaaga aaaaaggtat gtccggaggc atgtcaggaa gtgaagaagg tatgtctgga    1260
agtgaaggag gtatgtccgg aggtggagga ggtaaatcca aaagtagaaa aagtaaactc    1320
aaagctaaat tgggaaagaa aaaatgtatg tccggaggca tgtcaggaag tgaaggaggt    1380
atgtctggaa gtgaaggagg tatatccgga ggtggtatgt ctgggggcag tggaagtaaa    1440
cacaaaattg gaggaggtaa acacggaggt cttggaggta aattcggaaa gaaaagaggc    1500
atgtccggaa gtgaggagg catgtcagga agtgaaggag gtgtgtctgg aagtgaagga    1560
agtatgtctg gaggtggtat gtctgggggt agcggaagta acacaaaat ggaggaggt     1620
aaacacggag gtcttagagg taaattcgga agaaaaagg tatgtcagg aagtgaagga     1680
ggtatgtctg gaagtgaagg aggtatgtcg gaaagtggta tgtccgggag tggagggggt    1740
aaacacaaaa tcggaggagg taaacacaaa tttggaggag gtaaacacgg aggtggaggt    1800
ggccacatgg cggagtaa                                                  1818
```

<210> SEQ ID NO 2
<211> LENGTH: 1569
<212> TYPE: DNA
<213> ORGANISM: Arabidopsis thaliana

<400> SEQUENCE: 2

```
acaaagaaat taactatgaa acaatgcttt gtttaaatga agtaattaat cggtactata      60
gcgtatatac atagaatgga tccaatttaa ccaaagcaac tgtatgtgac tatgtgaatg     120
attcaatcgt gagacattga aattgtcgtt tctccattac cttttggaa gaaaaaccat      180
cgaaagctag ctaagacttt ttttattaaa cgaacttgct actatttcta tgttttcttt     240
gaaatgaaaa ttaaatttgt tactgtttca cctaaaactc aaaagtattg cttttaatt     300
ttattattaa gaaaaactaa tcttatttat gttaagaaac ctgtcaattt ttcattgtta     360
atttcggctc tataattatt aattaacaat caatttctca aaaattgcaa tcatgattat     420
gattagatat atattagttg gattgtgatg catttttgt aatataaaat ggatgtttgt      480
attagtttct cactcatgta attaaacacc aaatgctaga aactagtact tttgtttctc     540
agctctcgtc tattgttata tctgcaacac gaacaaaaac cttatctagg tgttatatat     600
cacggttatg tttatgagtt agaagggatt cttcaacaaa atcacgaaa ctacttgtat      660
atatgtatgt gtgtatccga tcgaggttga cttccggggt tggacgttga agaagacgaa     720
ttcattgatt gggcttatat atgggcatgt attacttggt tcaagtttgt aacacttta     780
gcttttcaa ttctattcga aaccaaaata ttgggctata tctttata caaccttcaa        840
gataaattgg accaatttta gaagagcaaa ttgaacccgg ccgttagcgt tagccaaacc     900
ccaactcctt ttcagtacaa ttaaatcaag aatttctaat aaatcgtgaa tttctagaca     960
tacatatcat aatttcgtca aagcgagcct acacctagtt ttgagctaca taactctttt    1020
cttttttttt ttatgattag gaggtttcaa aacccttgga cccataattt cttataatta    1080
gttttgtaat actaaattta ccattgagag cgacctctcg tcactagtaa ttcgaagatc    1140
tcatattcat gacctatatt aaccatcttc cagtcaagta atttcaatcg aaattcatca    1200
aaatcatata tttaacttag taatcacata tgatatggct aatatacgta atataacgat    1260
aaagatttct tcacgctttg atattccata aagcaatgga aatatggaat ggaagaaaac    1320
atttgaattt tacaagaaac aataaataga aggcctacaa acatgacaa cccacacaca     1380
cacacacgaa aagagaaaat ataagaagg acatgtaacg tgacgtagcg tagatctcca     1440
ttcactccaa tcgttttgca tggagcatgc atgtgtgtgt accgtgcacg tagtagagac    1500
cacacaactc cttcataaaa gccctctctc tcttaccatc accaaaacac aacaatccga    1560
tcagaaaat                                                           1569
```

<210> SEQ ID NO 3
<211> LENGTH: 543
<212> TYPE: PRT
<213> ORGANISM: Arabidopsis thaliana

<400> SEQUENCE: 3

```
Met Ser Glu Glu Leu Ser Gln Lys Pro Ser Ser Ala Gln Ser Leu Ser
1               5                   10                  15

Leu Arg Glu Gly Arg Asn Arg Phe Pro Phe Leu Ser Leu Ser Gln Arg
            20                  25                  30

Glu Gly Arg Phe Phe Pro Ser Leu Ser Leu Ser Glu Arg Asp Gly Arg
        35                  40                  45
```

```
Lys Phe Ser Phe Leu Ser Met Phe Ser Phe Leu Met Pro Leu Leu Glu
 50                  55                  60
Val Ile Lys Ile Ile Ile Ala Ser Val Ala Ser Val Ile Phe Val Gly
 65                  70                  75                  80
Phe Ala Cys Val Thr Leu Ala Gly Ser Ala Ala Leu Val Val Ser
                 85                  90                  95
Thr Pro Val Phe Ile Ile Phe Ser Pro Val Leu Val Pro Ala Thr Ile
                100                 105                 110
Ala Thr Val Val Leu Ala Thr Gly Phe Thr Ala Gly Ser Phe Gly
             115                 120                 125
Ala Thr Ala Leu Gly Leu Ile Met Trp Leu Val Lys Arg Arg Met Gly
            130                 135                 140
Val Lys Pro Lys Asp Asn Pro Pro Ala Gly Leu Pro Pro Asn Ser
145                 150                 155                 160
Gly Ala Gly Ala Gly Ala Gln Ser Leu Ile Lys Lys Ser Lys Ala
                165                 170                 175
Lys Ser Lys Gly Gly Leu Lys Ala Trp Cys Lys Lys Met Leu Lys Ser
                180                 185                 190
Lys Phe Gly Gly Lys Lys Gly Lys Ser Gly Gly Lys Ser Lys Phe
            195                 200                 205
Gly Gly Lys Gly Gly Lys Ser Glu Gly Glu Gly Met Ser Ser Gly
            210                 215                 220
Asp Glu Gly Met Ser Gly Ser Glu Gly Gly Met Ser Gly Gly Glu Gly
225                 230                 235                 240
Gly Lys Ser Lys Ser Gly Lys Gly Lys Leu Lys Ala Lys Leu Glu Lys
                245                 250                 255
Lys Lys Gly Met Ser Gly Gly Ser Glu Ser Glu Glu Gly Met Ser Gly
                260                 265                 270
Ser Glu Gly Gly Met Ser Gly Gly Gly Ser Lys Ser Lys Ser Lys
            275                 280                 285
Lys Ser Lys Leu Lys Ala Lys Leu Gly Lys Lys Gly Met Ser Gly
            290                 295                 300
Gly Met Ser Gly Ser Glu Glu Gly Met Ser Gly Ser Glu Gly Gly Met
305                 310                 315                 320
Ser Ser Gly Gly Gly Ser Lys Ser Lys Ser Lys Ser Lys Leu Lys
                325                 330                 335
Ala Lys Leu Gly Lys Lys Gly Met Ser Gly Gly Met Ser Gly Ser
            340                 345                 350
Glu Glu Gly Met Ser Gly Ser Glu Gly Gly Met Ser Gly Gly Gly Gly
                355                 360                 365
Gly Lys Ser Lys Ser Arg Lys Ser Lys Leu Lys Ala Lys Leu Gly Lys
            370                 375                 380
Lys Lys Cys Met Ser Gly Gly Met Ser Gly Ser Glu Gly Gly Met Ser
385                 390                 395                 400
Gly Ser Glu Gly Gly Ile Ser Gly Gly Met Ser Gly Gly Ser Gly
                405                 410                 415
Ser Lys His Lys Ile Gly Gly Gly Lys His Gly Gly Leu Gly Gly Lys
                420                 425                 430
Phe Gly Lys Lys Arg Gly Met Ser Gly Gly Gly Met Ser Gly
            435                 440                 445
Ser Glu Gly Gly Val Ser Gly Ser Glu Gly Ser Met Ser Gly Gly Gly
450                 455                 460
Met Ser Gly Gly Ser Gly Ser Lys His Lys Ile Gly Gly Gly Lys His
```

-continued

```
465                 470                 475                 480

Gly Gly Leu Arg Gly Lys Phe Gly Lys Lys Arg Gly Met Ser Gly Ser
                485                 490                 495

Glu Gly Gly Met Ser Gly Ser Glu Gly Gly Met Ser Glu Ser Gly Met
            500                 505                 510

Ser Gly Ser Gly Gly Gly Lys His Lys Ile Gly Gly Gly Lys His Lys
        515                 520                 525

Phe Gly Gly Gly Lys His Gly Gly Gly Gly Gly His Met Ala Glu
    530                 535                 540

<210> SEQ ID NO 4
<211> LENGTH: 33
<212> TYPE: DNA
<213> ORGANISM: Artificial Sequence
<220> FEATURE:
<223> OTHER INFORMATION: cDNA sequence (primer), sequence named as RR1f

<400> SEQUENCE: 4
ataaagcttt ttctctgttt ttgtccgtgg aac                                  33

<210> SEQ ID NO 5
<211> LENGTH: 34
<212> TYPE: DNA
<213> ORGANISM: Artificial Sequence
<220> FEATURE:
<223> OTHER INFORMATION: cDNA sequence (primer), sequence named as RR2r

<400> SEQUENCE: 5
ataccatggc acgtgattcg gtggaagtcc tgcc                                 34
```